(12) United States Patent
Kawashima et al.

(10) Patent No.: US 9,603,609 B2
(45) Date of Patent: Mar. 28, 2017

(54) ULTRASONIC TREATMENT SYSTEM, ENERGY SOURCE UNIT, AND ACTUATION METHOD OF ENERGY SOURCE UNIT

(71) Applicant: OLYMPUS CORPORATION, Hachioji-shi, Tokyo (JP)

(72) Inventors: Ko Kawashima, Musashino (JP); Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/216,331

(22) Filed: Jul. 21, 2016

(65) Prior Publication Data

US 2016/0325121 A1 Nov. 10, 2016

Related U.S. Application Data

(63) Continuation of application No. PCT/JP2015/067897, filed on Jun. 22, 2015.

(30) Foreign Application Priority Data

Jul. 24, 2014 (JP) ................................. 2014-151071

(51) Int. Cl.
*A61B 17/16* (2006.01)
*A61B 17/32* (2006.01)
(Continued)

(52) U.S. Cl.
CPC .. *A61B 17/1659* (2013.01); *A61B 17/320068* (2013.01); *A61B 18/00* (2013.01);
(Continued)

(58) Field of Classification Search
CPC ........ A61B 17/1659; A61B 17/320068; A61H 23/0245
See application file for complete search history.

(56) References Cited

U.S. PATENT DOCUMENTS 6,756,909 B2 * 6/2004 Wiener .......... A61B 17/320068
202/106
2002/0161385 A1 * 10/2002 Wiener .......... A61B 17/320068
606/169
(Continued)

FOREIGN PATENT DOCUMENTS

| JP | 2000-287989 A | 10/2000 |
| JP | 2004-298559 A | 10/2004 |
| JP | 2005-027907 A | 2/2005 |

OTHER PUBLICATIONS

Sep. 29, 2015 International Search Report issued in Patent Application No. PCT/JP2015/067897.

*Primary Examiner* — Andrew Yang
(74) *Attorney, Agent, or Firm* — Oliff PLC

(57) ABSTRACT

An energy supplier of an ultrasonic treatment system can output an electric power in a first output mode and a second output mode in which the electric power supplied to a drive force generation unit during a unit time is higher than in the first output mode. A controller maintains an output state of the electric power in the first output mode when a judgment section judges that a load on an ultrasonic probe is less than or equal to a threshold, and switches the output state of the electric power to the second output mode when the judgment section judges that the load is more than the first threshold.

15 Claims, 14 Drawing Sheets

(51) Int. Cl.
*A61B 18/00* (2006.01)
*A61H 23/02* (2006.01)
*A61N 7/00* (2006.01)

(52) U.S. Cl.
CPC .. *A61H 23/0245* (2013.01); *A61H 2201/5007* (2013.01); *A61H 2201/5058* (2013.01); *A61N 2007/0004* (2013.01)

(56) References Cited

U.S. PATENT DOCUMENTS

| | | | |
|---|---|---|---|
| 2005/0020967 A1* | 1/2005 | Ono | A61B 17/2202 604/22 |
| 2009/0318944 A1* | 12/2009 | Kimura | A61B 17/16 606/169 |
| 2010/0114184 A1* | 5/2010 | Degtyar | A61B 17/1659 606/86 R |
| 2010/0125292 A1* | 5/2010 | Wiener | A61B 17/320068 606/169 |
| 2015/0088154 A1* | 3/2015 | Vaitekunas | A61B 17/12 606/128 |
| 2016/0175000 A1* | 6/2016 | Akagane | A61B 18/14 606/169 |

* cited by examiner

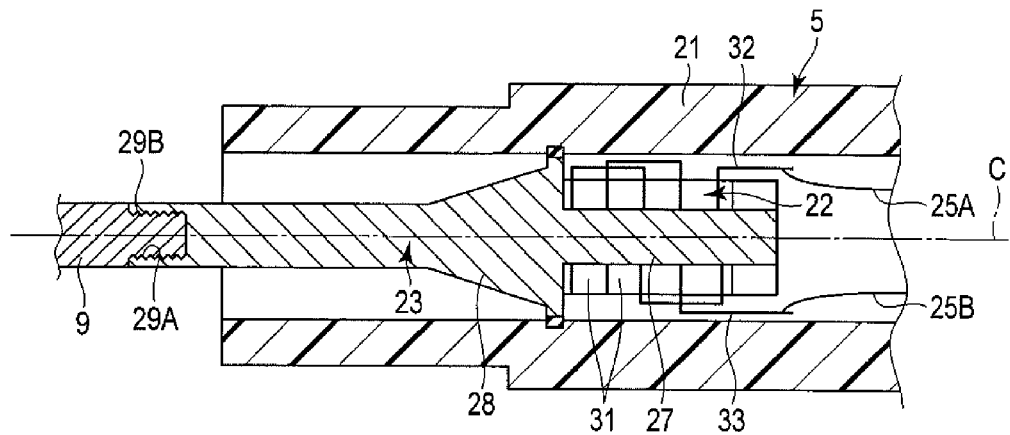
F I G. 2
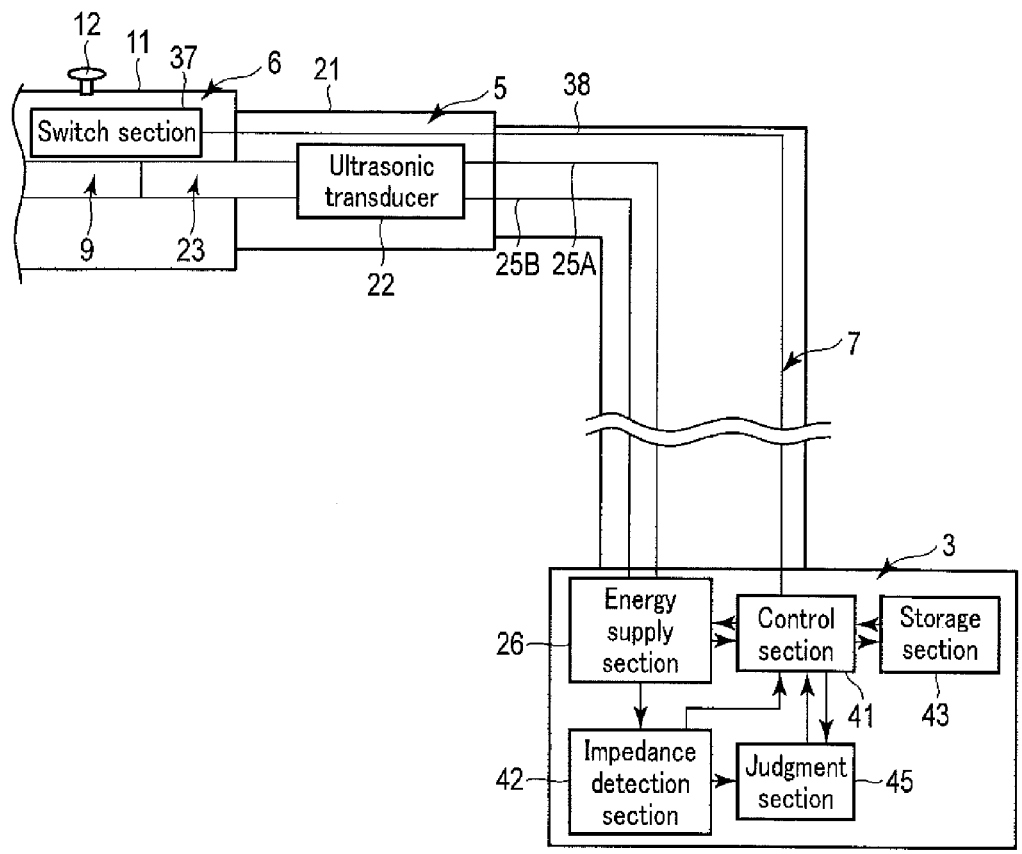
F I G. 3

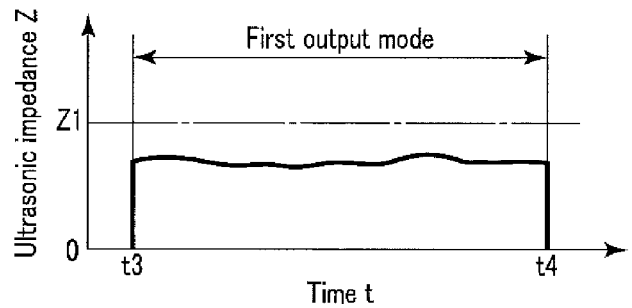
F I G. 7
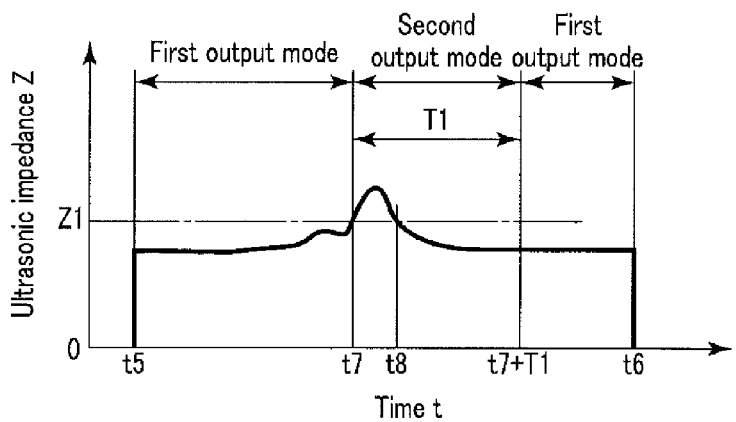
F I G. 8
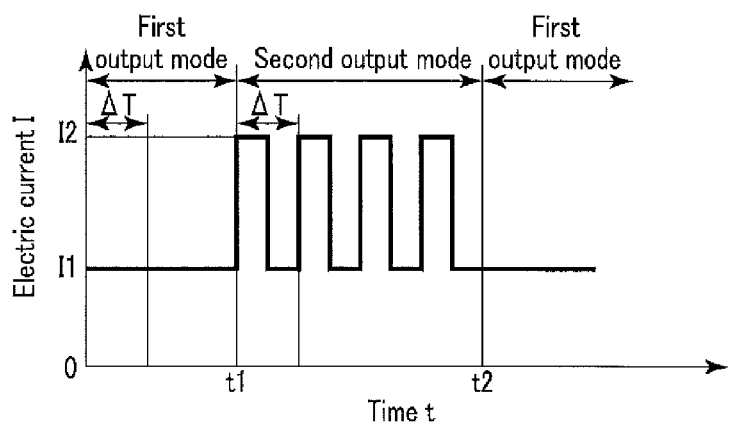
F I G. 9

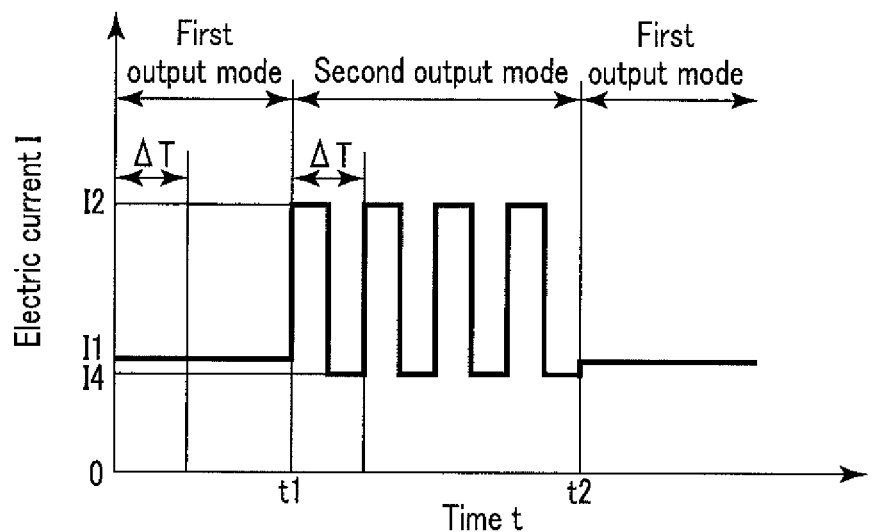
F I G. 10
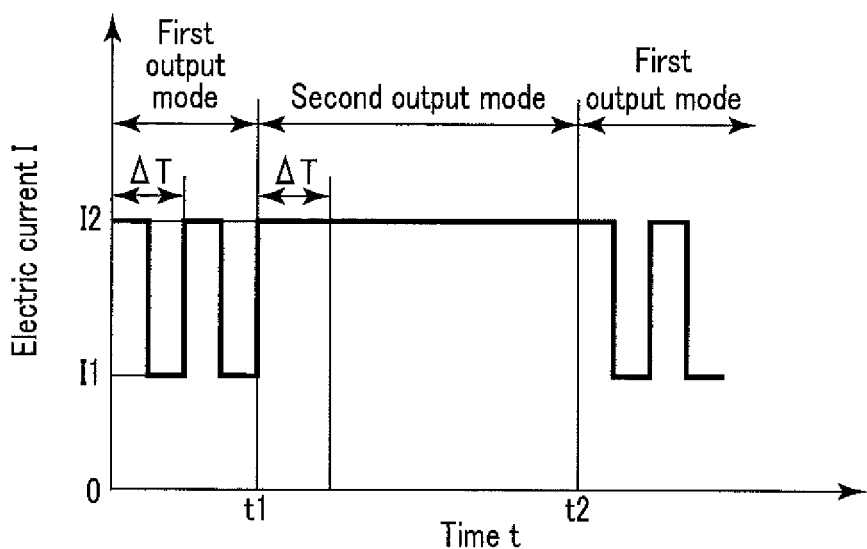
F I G. 11

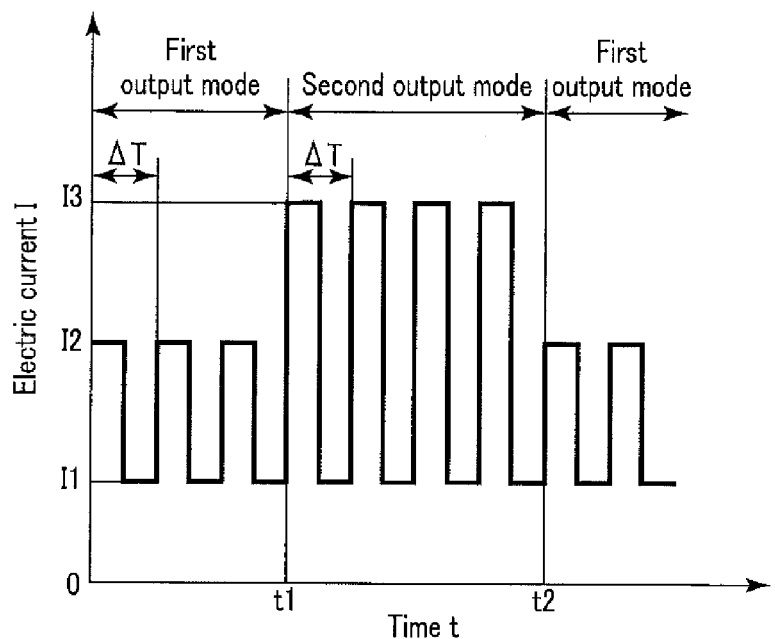
F I G. 12
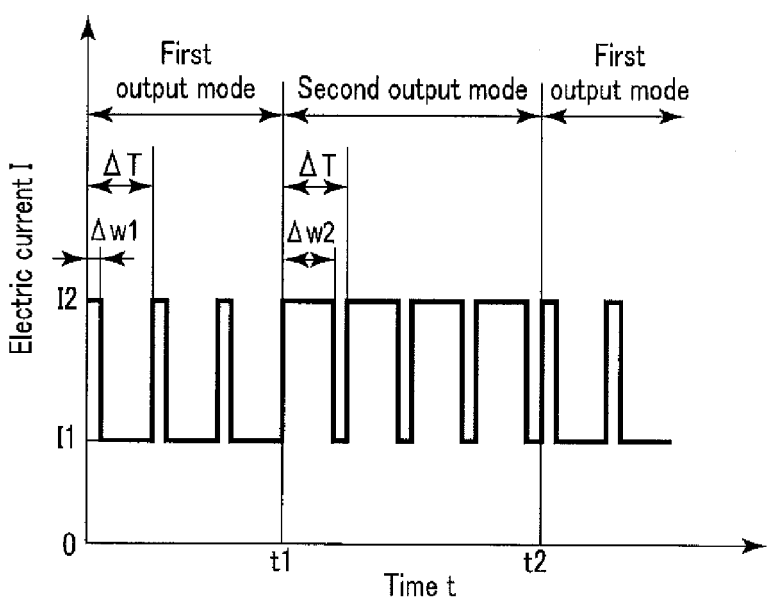
F I G. 13

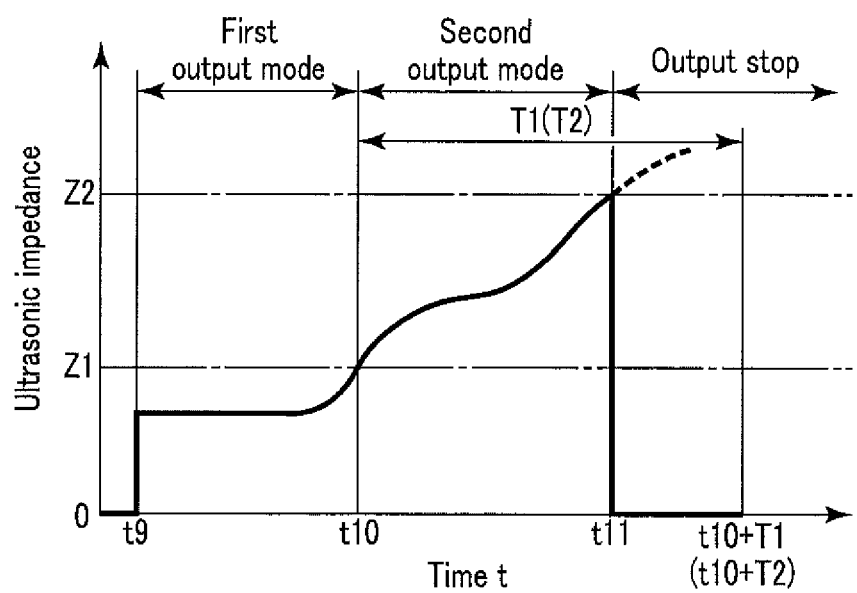
F I G. 15

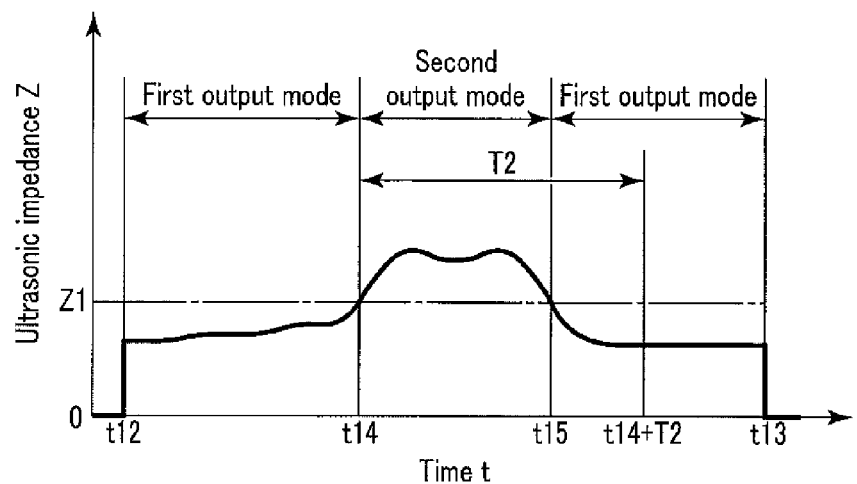
F I G. 17
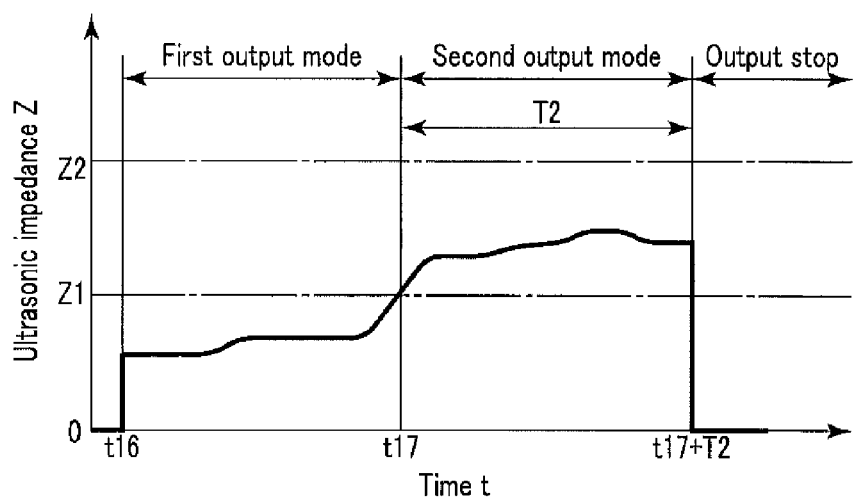
F I G. 18

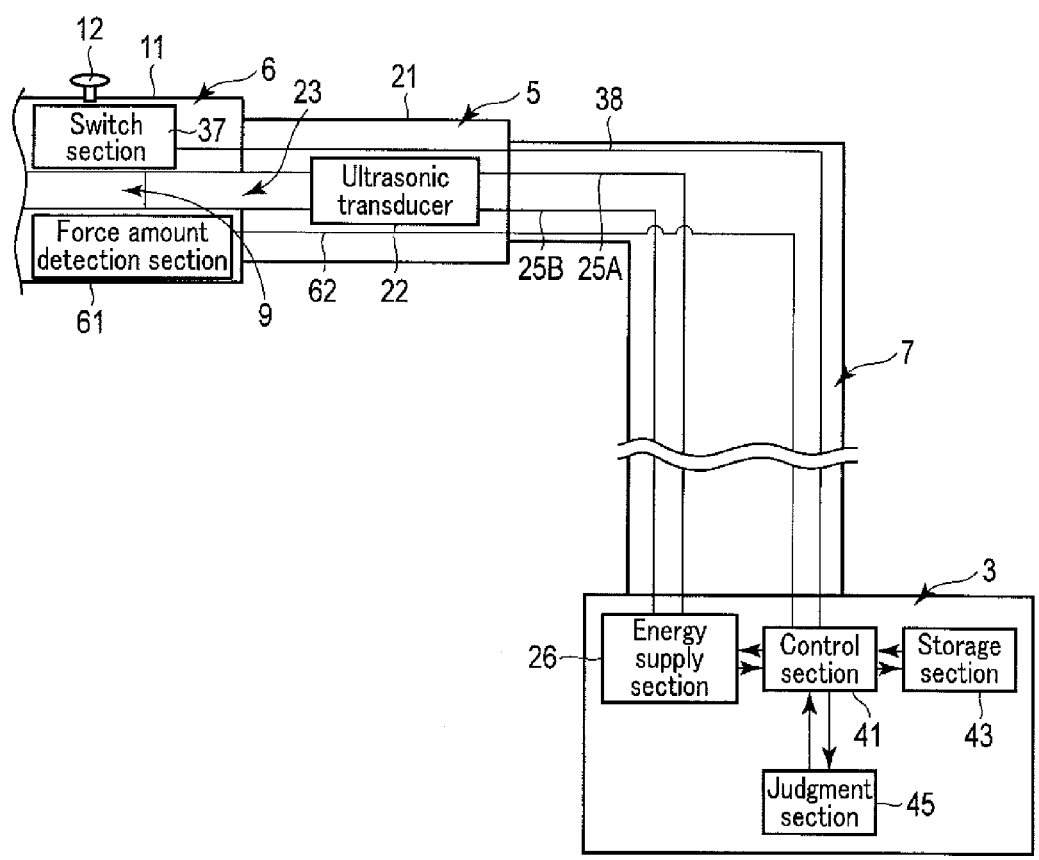
F I G. 23

ULTRASONIC TREATMENT SYSTEM, ENERGY SOURCE UNIT, AND ACTUATION METHOD OF ENERGY SOURCE UNIT

CROSS-REFERENCE TO RELATED APPLICATIONS

This is a Continuation Application of PCT Application No. PCT/JP2015/067897, filed Jun. 22, 2015 and based upon and claiming the benefit of priority from prior Japanese Patent Application No. 2014-151071, filed Jul. 24, 2014, the entire contents of which are incorporated herein by reference.

BACKGROUND OF THE INVENTION

1. Field of the Invention

The present invention relates to an ultrasonic treatment system including an ultrasonic treatment instrument to conduct a treatment by use of an ultrasonic vibration, and an energy source unit which supplies an electric power to actuate the ultrasonic treatment instrument, an energy source unit which supplies electric an electric power to actuate an ultrasonic treatment instrument, and an actuation method of an energy source unit.

2. Description of the Related Art

Jpn. Pat. Appln. KOKAI Publication No. 2005-27907 discloses an ultrasonic treatment system configured to transmit an ultrasonic vibration generated in an ultrasonic transducer to an ultrasonic probe, and configured to conduct a treatment with a treatment portion provided in a distal end of the ultrasonic probe. This ultrasonic treatment system detects an ultrasonic impedance on the basis of an electric power supplied to the ultrasonic transducer while the ultrasonic vibration is being generated in the ultrasonic transducer. The ultrasonic impedance changes in response to a load on the ultrasonic probe. When the electric power is supplied to the ultrasonic transducer, the ultrasonic impedance is compared with a set threshold (upper limit impedance). If the ultrasonic impedance becomes higher than the threshold, an electric current (the crest value of an alternating electric current) supplied to the ultrasonic transducer is reduced. Thus, the amplitude of the ultrasonic vibration (longitudinal vibration) generated in the ultrasonic transducer decreases.

BRIEF SUMMARY OF THE INVENTION

According to one aspect of the invention, an ultrasonic treatment system includes that: an ultrasonic probe which extends along a longitudinal axis, and which is configured to transmit an ultrasonic vibration, the ultrasonic probe including a treatment portion configured to conduct a treatment by use of the transmitted ultrasonic vibration; a drive force generation unit which includes a vibration generation section configured to generate the ultrasonic vibration, and which is configured to generate a drive force to actuate the ultrasonic probe; an energy supply section which is configured to output an electric power to generate the drive force in the drive force generation unit, the energy supply section having a first output mode and a second output mode, the electric power supplied to the drive force generation unit during a unit time being higher in the second output mode than in the first output mode; a load detection section which is configured to detect a load on the ultrasonic probe with time while the ultrasonic probe is transmitting the ultrasonic vibration; a judgment section which is configured to judge with time whether the load on the ultrasonic probe is less than or equal to a first threshold while the electric power is output from the energy supply section in the first output mode; and a control section, the control section being configured to maintain an output state of the electric power from the energy supply section in the first output mode when the judgment section judges that the load is less than or equal to the first threshold, the control section being configured to switch the output state of the electric power from the energy supply section to the second output mode when the judgment section judges that the load is more than the first threshold.

According to one another aspect of the invention, an energy source unit which is configured to supply an electric power to a drive force generation unit, the drive force generation unit being configured to generate a drive force to actuate an ultrasonic probe extending along a longitudinal axis, the energy source unit including: an energy supply section which is configured to generate an ultrasonic vibration that is transmitted to a treatment portion of the ultrasonic probe through the ultrasonic probe by supplying the electric power to a vibration generation section of the drive force generation unit, the energy supply section being configured to output the electric power in a first output mode and a second output mode, the electric power supplied to the drive force generation unit during a unit time being higher in the second output mode than in the first output mode; a load detection section which is configured to detect a load on the ultrasonic probe with time while the ultrasonic probe is transmitting the ultrasonic vibration; a judgment section which is configured to judge with time whether the load on the ultrasonic probe is less than or equal to a threshold while the electric power is output from the energy supply section in the first output mode; and a control section, the control section being configured to maintaining an output state of the electric power from the energy supply section in the first output mode when the judgment section judges that the load is less than or equal to the threshold, the control section being configured to switch the output state of the electric power from the energy supply section to the second output mode when the judgment section judges that the load is more than the threshold.

According to one another aspect of the invention, an actuation method of an energy source unit which supplies an electric power to a drive force generation unit, the drive force generation unit being configured to generate a drive force to actuate an ultrasonic probe extending along a longitudinal axis, the actuation method including: causing an energy supply section to generate an ultrasonic vibration that is transmitted to a treatment portion of the ultrasonic probe through the ultrasonic probe by supplying the electric power to a vibration generation section of the drive force generation unit; causing a load detection section to detect a load on the ultrasonic probe with time while the ultrasonic probe is transmitting the ultrasonic vibration; causing a judgment section to judge with time whether the load on the ultrasonic probe is less than or equal to a threshold while the electric power is output from the energy supply section in a first output mode; and causing a control section to control an output state of the electric power from the energy supply section on the basis of a judgment result in the judgment section, the control section maintaining the output state of the electric power from the energy supply section in the first output mode when the judgment section judges that the load is less than or equal to the threshold, the control section switching the output state of the electric power from the energy supply section to a second output mode when the judgment section judges that the load is more than the threshold, the electric power supplied to the drive force generation unit during a unit time being higher in the second output mode than in the first output mode.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view schematically showing the configuration of a transducer unit according to the first embodiment;

FIG. 3 is a schematic diagram showing an electric connection state in the transducer unit and an energy source unit according to the first embodiment;

FIG. 7 is a schematic diagram showing an example of changes of an ultrasonic impedance detected by an impedance detection section with time according to the first embodiment;

FIG. 8 is a schematic diagram showing an example of changes of the ultrasonic impedance detected by the impedance detection section with time according to the first embodiment which is different from that in FIG. 7;

FIG. 9 is a schematic diagram showing an example of changes of an electric current supplied from the energy supply section to the ultrasonic transducer with time according to a first modification of the first embodiment;

FIG. 10 is a schematic diagram showing an example of changes of the electric current supplied from the energy supply section to the ultrasonic transducer with time according to a second modification of the first embodiment;

FIG. 11 is a schematic diagram showing an example of changes of the electric current supplied from the energy supply section to the ultrasonic transducer with time according to a third modification of the first embodiment;

FIG. 12 is a schematic diagram showing an example of changes of the electric current supplied from the energy supply section to the ultrasonic transducer with time according to a fourth modification of the first embodiment;

FIG. 13 is a schematic diagram showing an example of changes of the electric current supplied from the energy supply section to the ultrasonic transducer with time according to a fourth modification of the first embodiment;

FIG. 15 is a schematic diagram showing an example of changes of the ultrasonic impedance detected by the impedance detection section with time according to the second embodiment which is different from that in each of FIG. 7 and FIG. 8;

FIG. 17 is a schematic diagram showing an example of changes of the ultrasonic impedance detected by the impedance detection section with time according to the third embodiment which is different from that in each of FIG. 7, FIG. 8, and FIG. 15;

FIG. 18 is a schematic diagram showing an example of changes of the ultrasonic impedance detected by the impedance detection section with time according to the third embodiment which is different from that in each of FIG. 7, FIG. 8, FIG. 15, and FIG. 17;

FIG. 23 is a schematic diagram showing an electric connection state in an ultrasonic treatment instrument and the energy source unit according to a certain modification of the first embodiment to the fifth embodiment.

DETAILED DESCRIPTION OF THE INVENTION

First Embodiment

Figure 1:
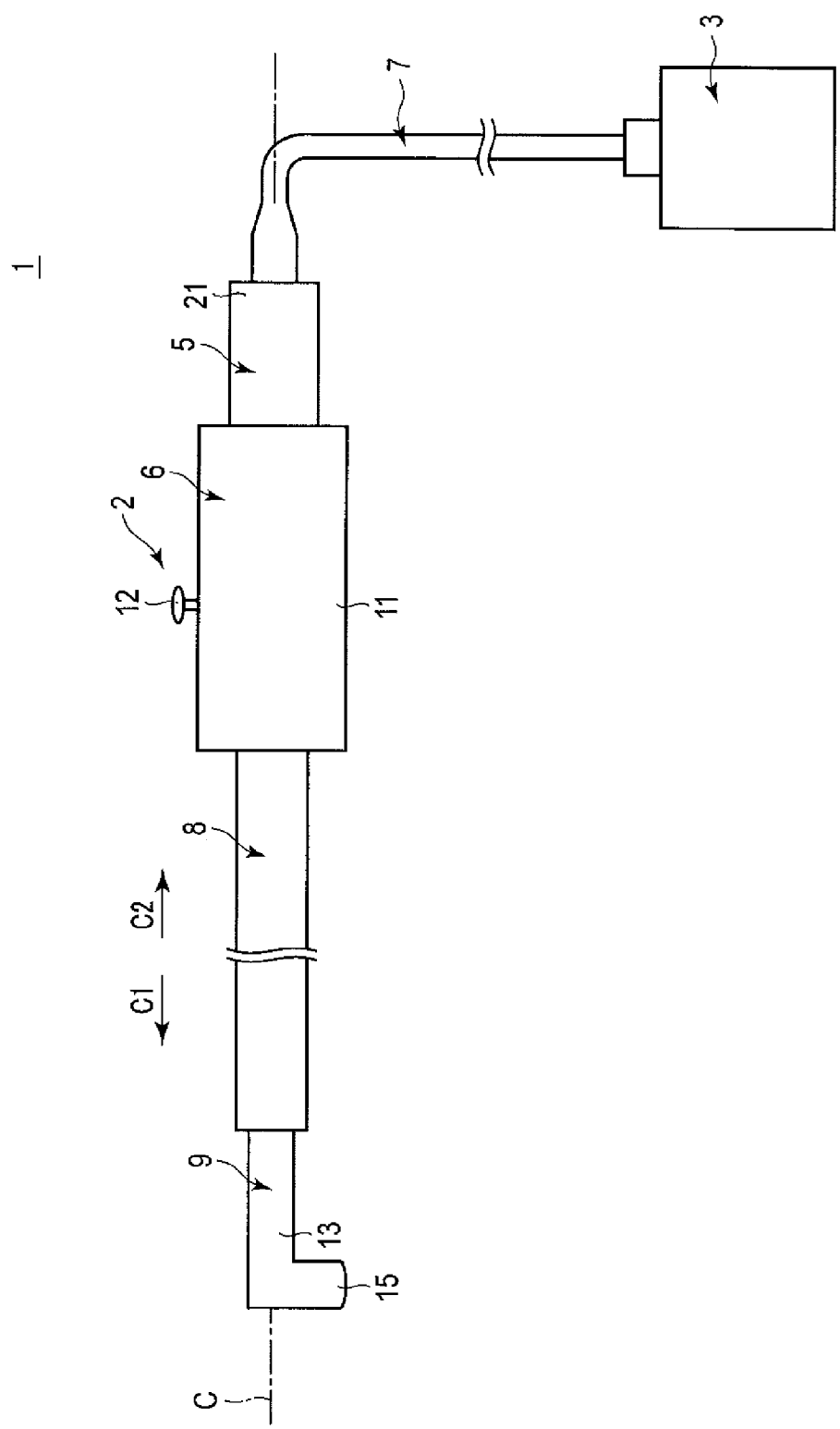
FIG. 1 is a schematic diagram showing an ultrasonic treatment system according to a first embodiment of the present invention.

A first embodiment of the present invention is described with reference to FIG. 1 to FIG. 8. FIG. 1 is a diagram showing an ultrasonic treatment system 1. As shown in FIG. 1, the ultrasonic treatment system 1 includes an ultrasonic treatment instrument (handpiece) 2, and an energy source unit (energy supply control unit) 3 which is configured to supply an electric power to the ultrasonic treatment instrument 2 as energy. The ultrasonic treatment instrument 2 has a longitudinal axis C. One side in a direction parallel to the longitudinal axis C is a distal direction (a direction of an arrow C1 in FIG. 1), and the side opposite to the distal direction is a proximal direction (a direction of an arrow C2 in FIG. 1). The ultrasonic treatment instrument 2 includes a transducer unit 5 and a holding unit (handle unit) 6. The vibrator unit 5 is detachably coupled to the proximal direction side of the holding unit 6. One end of a cable 7 is connected to a proximal portion of the transducer unit 5. The other end of the cable 7 is connected to the energy source unit 3. The energy source unit 3 is an electric power output device (energy output device) equipped with a processor including, for example, a central processing unit (CPU) or an application specific integrated circuit (ASIC).

The holding unit 6 includes a cylindrical case 11 extending along the longitudinal axis C. An energy operation input button 12 which is an energy operation input section is attached to the cylindrical case 11. The ultrasonic treatment instrument 2 includes a sheath 8 extending along the longitudinal axis C. The sheath 8 is inserted into the cylindrical case 11 from the distal direction side, and thereby attached to the holding unit 6. The ultrasonic treatment instrument 2 includes an ultrasonic probe 9. The ultrasonic probe 9 extends from the inside of the cylindrical case 11 through the inside of the sheath 8 along the longitudinal axis C. The ultrasonic probe 9 is inserted through the sheath 8. A treatment portion 13 protruding from a distal end of the sheath 8 toward the distal direction is provided in a distal portion of the ultrasonic probe 9. In the present embodiment, the treatment portion 13 is a substantially L-shaped hook provided with a protrusion 15 protruding toward one direction crossing to the longitudinal axis C.

The transducer unit 5 includes a transducer case 21. When the vibrator case 21 is inserted into the cylindrical case 11 from the proximal direction side, the transducer unit 5 is attached to the holding unit 6. Inside the cylindrical case 11, the vibrator case 21 is coupled into the sheath 8.

FIG. 2 is a diagram showing the configuration of the transducer unit 5. As shown in FIG. 2, the transducer unit 5 includes the transducer case 21 mentioned above, an ultrasonic transducer 22 which is a vibration generator provided inside the transducer case 21, and a horn component 23 to which the ultrasonic vibrator 22 is attached.

FIG. 3 is a diagram showing an electric connection state in the transducer unit 5 and the energy source unit 3. As shown in FIG. 2 and FIG. 3, one end of each of electric power supply paths 25A and 25B is connected to the ultrasonic transducer 22. The energy source unit 3 includes an energy supply section 26 configured to output an electric power (vibration generation electric power) P. The electric power supply paths 25A and 25B are formed from, for example, electric wires inside the transducer case 21 or electric wires inside the cable 7. The other ends of the electric power supply paths 25A and 25B are connected to the energy supply section 26. The energy supplier 26 includes, for example, an amplifier (amplification circuit) and a conversion circuit, and is configured to convert an electric power from an electric power supply (e.g. a battery or an outlet) into the output electric power P. The electric power (electric energy) P output from the energy supply section 26 is supplied to the ultrasonic transducer 22 via the electric power supply paths 25A and 25B. An ultrasonic vibration is generated in the ultrasonic vibrator 22 by the supply of the electric power P. In the present embodiment, the electric power P from the energy supply section 26 is supplied to the ultrasonic transducer 22 alone. The electric power P supplied to the ultrasonic transducer 22 is an alternating-current electric power.

The horn member 23 is provided with a transducer attachment portion 27 to which the ultrasonic transducer 22 is attached. The ultrasonic vibration generated in the ultrasonic vibrator 22 is transmitted to the horn component 23. The horn component 23 is also provided with a sectional area changing portion 28 located on the distal direction side with respect to the transducer attachment portion 27. In the sectional area changing portion 28, the sectional area perpendicular to the longitudinal axis C decreases toward the distal direction. The amplitude of the ultrasonic vibration is increased by the sectional area changing portion 28. An internal thread portion 29A is provided in a distal portion of the horn component 23. An external thread portion 29B is provided in a proximal portion of the ultrasonic probe 9. When the external thread portion 29B is screwed with the internal thread portion 29A, the ultrasonic probe 9 is connected to the distal direction side of the horn component 23. The ultrasonic probe 9 is connected to the horn member 23 inside the cylindrical case 11.

The ultrasonic vibration transmitted to the horn component 23 is transmitted toward the distal direction from the proximal direction along the longitudinal axis C in the horn component 23 and the ultrasonic probe 9. That is, a vibration transmission portion configured to transmit the generated ultrasonic vibration is formed by the horn component 23 and the ultrasonic probe 9. The ultrasonic vibration is transmitted toward the distal direction up to the treatment portion 13. The treatment portion 13 treats a treated target such as a living tissue by using the transmitted ultrasonic vibration.

In the present embodiment, while transmitting the ultrasonic vibration, the vibration transmission portion formed from the horn component 23 and the ultrasonic probe 9 makes longitudinal vibration in which a vibration direction is parallel to the longitudinal axis C (longitudinal direction) at a predetermined resonance frequency Fr. While the vibration transmission portion (the horn component 23 and the ultrasonic probe 9) is longitudinally vibrating at the predetermined resonance frequency Fr, the proximal end of the vibration transmission portion (the proximal end of the horn component 23) and the distal end of the vibration transmission portion (the distal end of the ultrasonic probe 9) are antinode positions of the longitudinal vibration. While the vibration transmission portion is longitudinally vibrating at the predetermined resonance frequency Fr, at least one node position of the longitudinal vibration is present between the proximal end and distal end of the vibration transmission portion. While the vibration transmission portion is longitudinally vibrating at the predetermined resonance frequency Fr, the antinode positions and at least one node position of the longitudinal vibration are fixed in number, and each of positions of the antinode and node positions of the longitudinal vibration in the longitudinal direction (i.e. the distal direction and the proximal direction) is fixed.

When the electric power (alternating-current electric power) P is supplied to the ultrasonic transducer 22 as described above, the ultrasonic probe 9 including the treatment portion 13 is actuated, and the ultrasonic probe 9 longitudinally vibrates. That is, in the ultrasonic transducer 22, the ultrasonic vibration is generated by the supply of the electric power P as drive force to actuate the ultrasonic probe 9. That is, in the present embodiment, a drive force generation unit configured to generate the drive force to actuate the ultrasonic probe 9 is formed by the ultrasonic transducer 22.

As shown in FIG. 2, the ultrasonic transducer 22 includes (in the present embodiment, four) ring-shaped piezoelectric elements 31. The vibrator attachment portion 27 of the horn component 23 is inserted through each of the piezoelectric elements 31. The ultrasonic transducer 22 also includes a first electrode portion 32 and a second electrode portion 33. One end of the electric power supply path 25A is connected to the first electrode portion 32, and one end of the electric power supply path 25B is connected to the second electrode portion 33.

Figure 4:
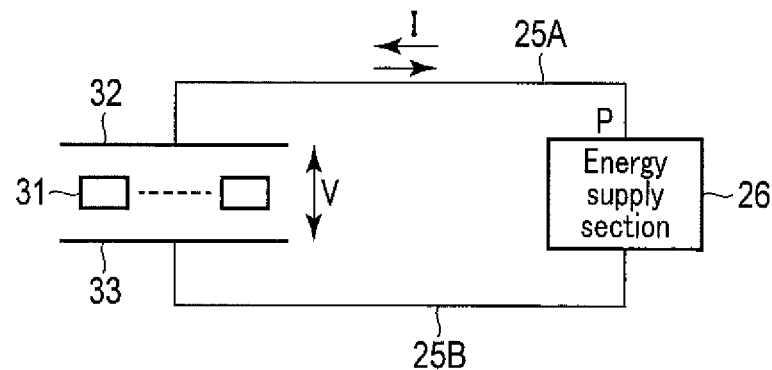
FIG. 4 is a schematic diagram showing an electric connection state between the transducer unit and an energy supply section according to the first embodiment.

FIG. 4 is a diagram showing an electric connection state between the ultrasonic transducer 22 and the energy supply section 26. As shown in FIG. 4, the energy supply section 26 and the first electrode portion 32 are electrically connected to each other by the electric power supply path 25A. The energy supply section 26 and the second electrode portion 33 are electrically connected to each other by the electric power supply path 25B. A voltage (vibration generation voltage) V is applied across the first electrode portion 32 and the second electrode portion 33 by the supply of the electric power (vibration generation electric power) P to the ultrasonic transducer 22 from the energy supply section 26. An electric current (vibration generation electric current) I flows through the piezoelectric elements 31 between the first electrode portion 32 and the second electrode portion 33 by the application of the voltage (alternating-current voltage) V. The electric current I is an alternating electric current, and the direction of the electric current periodically changes. The amplitude of the longitudinal vibration resulting from the ultrasonic vibration in the ultrasonic probe 9 including the treatment portion 13 is proportional to the intensity of the electric current I supplied to the piezoelectric elements 31 (i.e. the crest value of the alternating electric current I). An ultrasonic impedance (acoustic impedance) Z which is the impedance of the electric power P is as follows:

[Equation 1]

$$Z = V/I = V^2/P \qquad (1)$$

In the present embodiment, the electric current I flowing through the piezoelectric elements 31 is a sinusoidal alternating electric current. Therefore, while the electric power P is being supplied to the ultrasonic transducer 22, the crest factor of the electric current I (i.e. a value in which the crest value (maximum value) is divided by an effective value) is constantly a second root of 2 ($\sqrt{2}$) with time. The electric current I is a continuous-wave electric current which continuously flows through the piezoelectric elements 31 with time. Therefore, while the electric power P is being supplied, the ultrasonic vibration is continuously generated in the ultrasonic vibrator 22 with time. The electric current I may be, for example, a square-wave alternating electric current or a triangular-wave alternating electric current instead of the sinusoidal alternating electric current.

As shown in FIG. 3, the energy source unit (energy supply control unit) 3 includes a control section 41 electrically connected to the energy supply section 26. A switch section 37 is provided inside the cylindrical case 11. The switch section 37 is turned on or off by the energy operation input button 12 on the basis of an input of an energy operation. The switch section 37 is connected to the controller 41 via a signal path portion 38 which extends through the transducer case 21 and the inside of the cable 7. When the switch section 37 is turned on, an operation signal is transmitted to the control section 41 via the signal path portion 38. On the basis of the transmitted operation signal, the control section 41 controls the output state of the electric power P from the energy supplier 26. The control section 41 is formed from a processor including, for example, a CPU or an ASIC.

The energy source unit 3 also includes an impedance detection section 42. This impedance detection section 42 is formed from electronic circuits such as an electric current detection circuit, a voltage detection circuit, and a calculation circuit provided in the processor that constitutes the control section 41. The impedance detector 42 configured to detect the ultrasonic impedance Z of the electric power P with time while the electric power P is being supplied to the ultrasonic transducer 22 from the energy supply section 26. The impedance detection section 42 is configured to detect changes of the electric current (vibration generation electric current) I and the voltage (vibration generation voltage) V with time on the basis of the output state of the electric power P from the energy supply section 26. Equation (1) mentioned above is then used to detect changes of the ultrasonic impedance Z with time.

Here, the ultrasonic impedance Z changes in accordance with the load on the ultrasonic probe 9, and the ultrasonic impedance Z also increases if the load on the ultrasonic probe 9 increases. Therefore, the load on the ultrasonic probe 9 is detected with time by detecting the ultrasonic impedance Z with time. That is, the impedance detection section 42 constitutes a load detection section which is configured to detect the load on the ultrasonic probe 9 while the electric power P is being supplied to the ultrasonic transducer 22 (i.e. while the ultrasonic probe 9 is transmitting a vibration). The control section 41 controls the output state of the electric power P from the energy supply section 26 on the basis of the changes of the ultrasonic impedance Z with time detected by the impedance detector 42 (i.e. the changes of the load on the ultrasonic probe 9 with time).

A storage section 43 such as a memory is provided in the energy source unit 3. Information regarding characteristics of the ultrasonic treatment instrument 2, control programs for the energy supply section 26 by the control section 41, and others are stored in the storage section 43. A judgment section 45 is also provided in the energy source unit 3. This judgment section 45 is formed from an electronic circuit such as a judgment circuit provided in the processor that constitutes the controller 41. The judgment section 45 is configured to judge with time whether the ultrasonic impedance Z is less than or equal to a threshold (first threshold) Z1 while the impedance detection section 42 is detecting the ultrasonic impedance Z (i.e. the load on the ultrasonic probe 9). That is, the judgment section 45 judges with time whether the ultrasonic impedance Z is less than or equal to a threshold Z1 while the electric power P is being output from the energy supply section 26 (i.e. while an ultrasonic vibration is being generated in the ultrasonic transducer 22). The threshold Z1 may be stored in the storage section 43 or may be set by, for example, a surgeon using a setting input section (not shown) provided in the energy source unit 3. The control section 41 may take charge of the functions of the impedance detection section 42 and the judgment section 45 mentioned above.

Next, the functions and advantageous effects of the ultrasonic treatment system 1 and the energy source unit 3 are described. The ultrasonic treatment system 1 is used, for example, in a treatment to shave a hard tissue such as a bone. When the ultrasonic treatment system 1 is used to conduct a treatment, the sheath 8 and the ultrasonic probe 9 are inserted into, for example, a body cavity in which a treated target (hard tissue) is located. A protruding end of the protrusion 15 of the treatment portion 13 is then brought into contact with the hard tissue. If an energy operation is input by the energy operation input button 12 in this state, an operation signal is transmitted to the control section 41, and the output of the electric power (vibration generation electric power) P from the energy supply section 26 is started. The electric power P is supplied to the ultrasonic transducer (drive force generation unit) 22, so that the electric current (vibration generation electric current) I is converted into an ultrasonic vibration by the piezoelectric elements 31.

The generated ultrasonic vibration is then transmitted to the ultrasonic probe 9 via the horn component 23, and the ultrasonic vibration is transmitted toward the distal direction from the proximal direction in the ultrasonic probe 9. As a result, the ultrasonic probe 9 including the treatment portion 13 longitudinally vibrates. The hard tissue is abraded by the longitudinal vibration of the treatment portion 13 while the protruding end of the protrusion 15 is in contact with the treated target (hard tissue).

Figure 5:
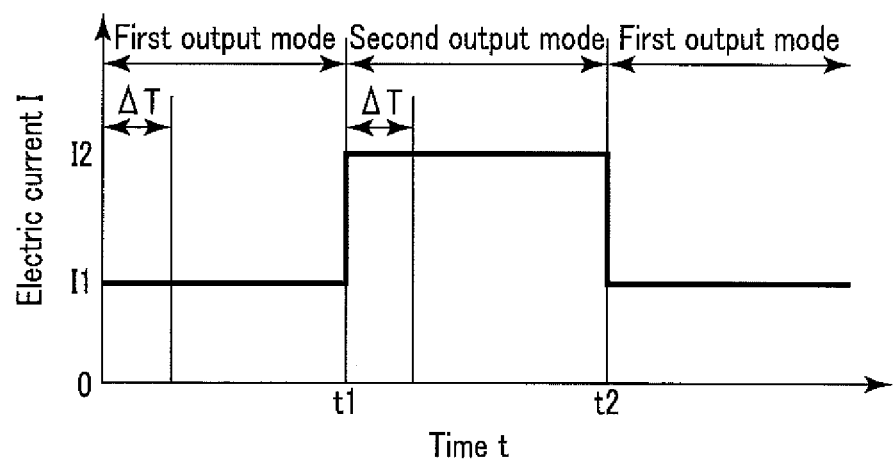
FIG. 5 is a schematic diagram showing an example of changes of an electric current supplied from the energy supply section to the ultrasonic transducer with time according to the first embodiment.

Here, the energy supply section 26 can output the electric power P in a first output mode and a second output mode. FIG. 5 shows an example of changes of the electric current (vibration generation electric current) I supplied from the energy supply section 26 to the ultrasonic transducer (drive force generation unit) 22 with time. FIG. 5 shows the changes of the crest value of the electric current (alternating electric current) I with time, in which (the crest value of) the electric current I is indicated on the vertical axis, and time t is indicated on the horizontal axis. In the example of FIG. 5, the electric power P (first electric power) is output in the first output mode before a time t1 and after a time t2, and the electric power P (second electric power) is output in the second output mode between the time t1 and the time t2.

As shown in FIG. 5, in the first output mode of the energy supply section 26, the electric current I supplied to the ultrasonic transducer (drive force generation unit) 22 continuously has a first crest value (first maximum value) I1 with time. That is, in the first output mode, the control section 41 controls the output state of the electric power P from the energy supply section 26 under constant current control in which the electric current I is constantly kept at the first crest value (first amplitude) I1 with time. Therefore, the voltage V (the electric power P) is adjusted in response to the changes of the ultrasonic impedance Z detected by the impedance detection section 42 with time so that the electric current (vibration generation electric current) I will constantly have the first crest value I1 with time. For example, if the ultrasonic impedance Z increases, the voltage V (the electric power P) is increased in response to the increase of the ultrasonic impedance Z so that the electric current I is kept at the first crest value I1 with time.

In the second output mode of the energy supply section 26, the electric current I supplied to the ultrasonic transducer (drive force generation unit) 22 continuously has a second crest value (second maximum value) I2 higher than the first crest value I1 with time. That is, in the second output mode, the control section 41 controls the output state of the electric power P from the energy supply section 26 under constant current control in which the electric current I is constantly kept at the second crest value (second amplitude) I2 with time. Therefore, the voltage V (the electric power P) is adjusted in response to the changes of the ultrasonic impedance Z detected by the impedance detection section 42 with time so that the electric current (vibration generation electric current) I will continuously have the second crest value I2 with time.

As described above, the second crest value I2 of the electric current I supplied to the ultrasonic transducer 22 in the second output mode is higher than the first crest value I1 of the electric current I supplied to the ultrasonic transducer 22 in the first output mode. Thus, the electric current I supplied to the ultrasonic vibrator (drive force generation unit) 22 during a unit time ΔT is higher in the second output mode than in the first output mode. Therefore, the electric power P supplied to the ultrasonic vibrator (drive force generation unit) 22 during the unit time ΔT is higher in the second output mode than in the first output mode due to, for example, the relation shown in Equation (1) mentioned above.

The amplitude of the longitudinal vibration in the ultrasonic probe 9 including the treatment portion 13 is proportional to the crest value of the electric current I supplied to the ultrasonic transducer 22. Therefore, the second crest value I2 of the electric current I in the second output mode is higher than the first crest value I1 of the electric current I in the first output mode, so that amplitude U2 of the longitudinal vibration in the treatment portion 13 in the second output mode is larger than amplitude U1 of the longitudinal vibration in the treatment portion 13 (e.g. the protruding end of the protrusion 15) in the first output mode of the energy supply section 26. Consequently, a movement distance (movement amount) of the treatment portion 13 (e.g. the protruding end of the protrusion 15) in the longitudinal direction parallel to the longitudinal axis C during the unit time ΔT is greater in the second output mode of the energy supply section 26 than in the first output mode.

Figure 6:
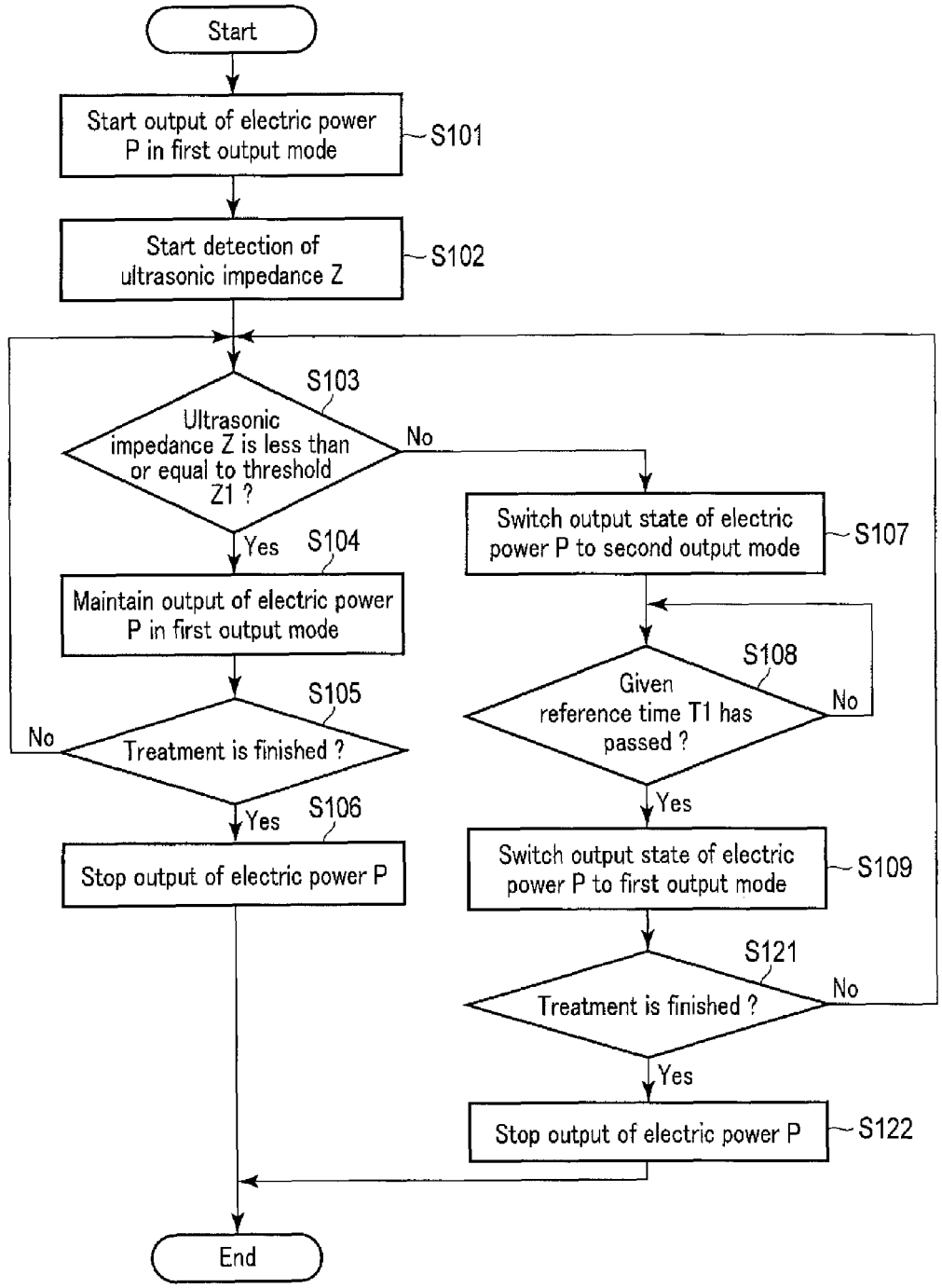
FIG. 6 is a flowchart showing processing in a treatment by the energy source unit according to the first embodiment.

FIG. 6 is a flowchart showing processing in the energy source unit 3 in a treatment (a treatment to shave a hard tissue). As described above, in the treatment, the electric power P is output from the energy supply section 26 on the basis of the input of the energy operation while the treatment portion 13 (e.g. the protruding end of the protrusion 15) is in contact with the hard tissue. As shown in FIG. 6, when the treatment is conducted, the energy supply section 26 first starts the output of the electric power (vibration generation energy) P in the first output mode mentioned above (step S101). As a result, the ultrasonic vibration is generated in the ultrasonic transducer 22, and the generated ultrasonic vibration is transmitted to the treatment portion 13 through the ultrasonic probe 9. If the output of the electric power P is started, the impedance detection section 42 starts the detection of the ultrasonic impedance Z (step S102). Accordingly, the ultrasonic impedance Z is detected with time while the electric power P is being output in the first output mode. Owing to the detection of the ultrasonic impedance Z with time, the load on the ultrasonic probe 9 is detected with time while the ultrasonic probe 9 is transmitting the ultrasonic vibration.

While the electric power P is being output from the energy supply section 26 in the first output mode, the judgment section 45 judges with time whether the ultrasonic impedance Z is less than or equal to the threshold (first threshold) Z1 (step S103). As a result, it is judged with time whether the load on the ultrasonic probe 9 is less than or equal to the threshold (first threshold) while the electric power P is being output in the first output mode. When the judgment section 45 judges that the ultrasonic impedance Z is less than or equal to the threshold Z1 (step S103—yes), the control section 41 maintains the output state of the electric, power P from the energy supply section 26 in the first output mode (step S104). When the treatment is continued (step S105—no), the processing returns to step S103, and the judgment section 45 judges with time whether the ultrasonic impedance Z is less than or equal to the threshold Z1.

When the treatment is finished (step S105—yes), the energy operation input button 12 is released, and the input of the energy operation in the energy operation input button 12 is stopped. Accordingly, the output (supply) of the electric power P to the ultrasonic transducer (drive force generation unit) 22 from the energy supply section 26 is stopped (step S106).

FIG. 7 is a diagram showing an example of changes of the ultrasonic impedance Z detected by the impedance detection section 42 with time. In FIG. 7, the ultrasonic impedance Z is indicated on the vertical axis, and time t is indicated on the horizontal axis. In FIG. 7, the output of the electric power P from the energy supply section 26 is started at a time t3, and the output of the electric power P from the energy supply section 26 is stopped at a time t4.

As shown in FIG. 7, for example, when a treatment is conducted so that the protrusion 15 of the treatment portion 13 does not bite into (is not caught in) a treated target such as a hard tissue during the treatment (i.e. while the energy supply section 26 is outputting the electric power P), the ultrasonic impedance Z is continuously less than or equal to the threshold Z1 with time. That is, the ultrasonic impedance Z is always less than or equal to the threshold Z1 from the time t3 to the time t4 in which the energy supply section 26 outputs the electric power P. Thus, from the time t3 to the time t4, the controller 41 controls the energy supply section 26 so that the electric power P is output from the energy supply section 26 in the first output mode.

When the judgment section 45 judges in step S103 of FIG. 6 that the ultrasonic impedance Z is more than the threshold Z1 (step S103—no), the control section 41 switches the output state of the electric power P from the energy supply section 26 from the first output mode to the second output mode (step S107). Until a given reference time T1 passes after the switch of the output state of the electric power P to the second output mode (step S108—no), the output of the electric power P from the energy supply section 26 in the second output mode is maintained by the control section 41.

At the time (point) when the given reference time T1 has passed since the switch of the output state of the electric power P from the energy supply section 26 to the second output mode (step S108—yes), the control section 41 switches the output state of the electric power P from the energy supply section 26 from the second output mode to the first output mode (step S109). If the output mode is switched to the first output mode in step S109 and when the treatment is continued (step S121—no), the processing returns to step S103, and the judgment section 45 judges with time whether the ultrasonic impedance Z is less than or equal to the threshold Z1. The given reference time T1 is, for example, 0.5 seconds to 1.0 second.

When the treatment is finished in step S121 (step S121—yes), the input of the energy operation in the energy operation input button 12 is stopped. Accordingly, the output (supply) of the electric power P to the ultrasonic transducer (drive force generation unit) 22 from the energy supply section 26 is stopped (step S122).

FIG. 8 is a diagram showing an example of changes of the ultrasonic impedance Z detected by the impedance detection section 42 with time which is different from that in FIG. 7. In FIG. 8, the ultrasonic impedance Z is indicated on the vertical axis, and time t is indicated on the horizontal axis. In FIG. 8, the output of the electric power P from the energy supply section 26 is started at a time t5, and the output of the electric power P from the energy supply section 26 is stopped at a time t6.

In a treatment to abrade a hard tissue such as a bone by the treatment portion 13 which is vibrated by the ultrasonic vibration, the treatment portion 13 (the protrusion 15 in particular) may bite into (may be caught in) the hard tissue. When the treatment portion 13 has bitten in the hard tissue, the load on the ultrasonic probe 9 is greater. Thus, the ultrasonic impedance Z of the electric power P supplied to the ultrasonic transducer (vibration generation section) 22 is higher.

In FIG. 8, from the time t5 at which the output of the electric power P from the energy supply section 26 is started to the time t7, the ultrasonic impedance Z is less than or equal to the threshold Z1. However, in FIG. 8, in the vicinity of the time t7, the treatment portion 13 bites into the hard tissue (treated target), and the ultrasonic impedance Z increases. As a result, at the time t7, the ultrasonic impedance Z becomes higher than the threshold Z1. Because the ultrasonic impedance Z becomes higher than the threshold Z1, the control section 41 switches the output state of the electric power P from the energy supply section 26 from the first output mode to the second output mode on the basis of the judgment in the judgment section 45 at the time t7.

As described above, the electric current I (electric power P) supplied to the ultrasonic transducer 22 during the unit time ΔT is higher in the second output mode than in the first output mode. The amplitude U2 of the longitudinal vibration in the treatment portion 13 in the second output mode is higher than the amplitude U1 of the longitudinal vibration in the treatment portion 13 in the first output mode, and the movement distance (movement amount) of the treatment portion 13 in the longitudinal direction parallel to the longitudinal axis C during the unit time ΔT is greater in the second output mode than in the first output mode. Because the movement distance of the treatment portion 13 during the unit time ΔT is greater, the treatment portion 13 changes from the state in which the treatment portion 13 has bitten in the hard tissue, and the biting of the treatment portion 13 into the hard tissue is more easily eliminated.

In FIG. 8, the biting of the treatment portion 13 into the hard tissue is eliminated in the vicinity of the time t8, and the ultrasonic impedance Z becomes less than or equal to the threshold Z1 at the time t8. After the time t8, the ultrasonic impedance Z is always less than or equal to the threshold Z1 up to the time t6 at which the output of the electric power P is stopped. In FIG. 8, the output state of the electric power P is maintained in the second output mode until the given reference time T1 passes from the time t7 at which the output of the electric power P is switched to the second output mode. At the time t7+T1 when the given reference time T1 has passed since the time t7, the output state of the electric power P from the energy supply section 26 is switched to the first output mode from the second output mode. In one example of FIG. 8, the time t7+T1 to switch to the first output mode is later than the time t8 at which the ultrasonic impedance Z becomes less than or equal to the threshold Z1.

As described above, in the present embodiment, the output state of the electric power P from the energy supply section 26 is switched between the first output mode and the second output mode on the basis of the changes of the ultrasonic impedance Z (the load on the ultrasonic probe 9) with time. Therefore, even when the treatment portion 13 has bitten in (has been caught in) the hard tissue, the biting of the treatment portion 13 into the hard tissue is appropriately eliminated.

Modifications of First Embodiment

The output state of the electric power P in each of the first output mode and the second output mode is not limited to the output state according to the first embodiment. First to fifth modifications in which the output state of the electric power P in each of the first output mode and the second output mode is different from that according to the first embodiment are described. Each of FIG. 9 to FIG. 13 shows an example of changes of the electric current (vibration generation electric current) I supplied from the energy supply section 26 to the ultrasonic transducer (drive force generation unit) 22 with time in the corresponding modification. In each of FIG. 9 to FIG. 13, the electric current I is indicated on the vertical axis, and time t is indicated on the horizontal axis, to show changes of the crest value of the electric current (alternating electric current) I with time. In each of FIG. 9 to FIG. 13, the electric power P is output in the first output mode before the time t1 and after time t2, and the electric power P is output in the second output mode between the time t1 and time t2.

In the first modification shown in FIG. 9, as in the first embodiment, the electric current I supplied to the ultrasonic transducer (vibration generation section) 22 continuously has the first crest value (first maximum value) I1 with time in the first output mode of the energy supply section 26. However, according to the present modification, in the second output mode, the electric current I supplied to the ultrasonic transducer 22 alternately changes to the first crest value (first amplitude) I1 and the second crest value (second amplitude) I2 higher than the first crest value I1 with time. That is, in the second output mode, the electric current I periodically changes between the state to have the first crest value I1 and the state to have the second crest value I2. Thus, in the second output mode, the electric current supplied to the ultrasonic vibrator 22 intermittently has the first crest value I1 and intermittently has the second crest value I2 higher than the first crest value I1. In the second output mode, the control section 41 controls the output state of the electric power P from the energy supply section 26 by alternately repeating the state to perform the constant current control in which the electric current I is constantly kept at the first crest value (first amplitude) I1 with time and the state to perform the constant current control in which the electric current I is constantly kept at the second crest value (second amplitude) I2 with time.

As described above, the electric current I continuously has the first crest value I1 with time in the first output mode, whereas the electric current I supplied to the ultrasonic transducer 22 intermittently has the second crest value I2 higher than the first crest value I1 in the second output mode. Thus, the electric current I supplied to the ultrasonic vibrator (vibration generator) 22 during the unit time ΔT is higher in the second output mode than in the first output mode. Therefore, the electric power P supplied to the ultrasonic transducer (drive force generation unit) 22 during the unit time ΔT is higher in the second output mode than in the first output mode due to, for example, the relation shown in Equation (1) mentioned above.

The amplitude of the longitudinal vibration in the treatment portion 13 (e.g. the protruding end of the protrusion 15) is larger in the state in which the electric current I has the second crest value I2 than in the state in which the electric current I has the first crest value I1. Therefore, the movement distance (movement amount) of the treatment portion 13 in the longitudinal direction parallel to the longitudinal axis C during the unit time ΔT is greater in the second output mode in which the electric current I intermittently has the second crest value I2 than in the first output mode.

In the second modification shown in FIG. 10, in the second output mode, the electric current I supplied to the ultrasonic transducer 22 alternately changes to the second crest value (second amplitude) I2 higher than the first crest value (first amplitude) I1 and a crest value (amplitude) I4 lower than the first crest value I1. That is, in the second output mode, the electric current I periodically changes between the state to have the second crest value I2 and the state to have the crest value I4. Thus, in the second output mode, the electric current I supplied to the ultrasonic vibrator 22 intermittently has the crest value I4 and intermittently has the second crest value I2 higher than the first crest value I1. In the second output mode, the control section 41 controls the output state of the electric power P from the energy supplier 26 by alternately repeating with time the state to perform the constant current control in which the electric current I is constantly kept at the crest value (amplitude) I4 with time and the state to perform the constant current control in which the electric current I is constantly kept at the second crest value (second amplitude) I2 with time.

Here, the difference between the first crest value I1 and the crest value I4 is extremely smaller than the difference between the second crest value I2 and the first crest value I1. Thus, the electric current I supplied to the ultrasonic transducer (vibration generation section) 22 during the unit time ΔT is higher in the second output mode in which the electric current I supplied to the ultrasonic transducer 22 intermittently has the second crest value I2 higher than the first crest value I1 than in the first output mode in which the electric current I continuously has the first crest value I1 with time. Therefore, the electric power P supplied to the ultrasonic vibrator (drive force generation unit) 22 during the unit time ΔT is higher in the second output mode than in the first output mode due to, for example, the relation shown in Equation (1) mentioned above.

The amplitude of the longitudinal vibration in the treatment portion 13 (e.g. the protruding end of the protrusion 15) is larger in the state in which the electric current I has the second crest value I2 than in the state in which the electric current I has the first crest value I1. The difference between the amplitude U1 of the longitudinal vibration in the treatment portion 13 in which the electric current has the first crest value I1 and amplitude U4 of the longitudinal vibration in the treatment portion 13 in which the electric current has the crest value I4 is much smaller than the difference between the amplitude U2 of the longitudinal vibration in the treatment portion 13 in which the electric current has the second crest value I2 and the amplitude U1 of the longitudinal vibration. Therefore, the movement distance (movement amount) of the treatment portion 13 in the longitudinal direction parallel to the longitudinal axis C during the unit time ΔT is greater in the second output mode in which the electric current I intermittently has the second crest value I2 than in the first output mode.

In the third modification shown in FIG. 11, in the first output mode of the energy supply section 26, the electric current I supplied to the ultrasonic transducer 22 alternately changes to the first crest value (first amplitude) I1 and the second crest value (second amplitude) I2 higher than the first crest value I1 with time. That is, in the first output mode, the electric current I periodically changes between the state to have the first crest value I1 and the state to have the second crest value I2. In the first output mode, the control section 41 controls the output state of the electric power P from the energy supply section 26 by alternately repeating with time the state to perform the constant current control in which the electric current I is constantly kept at the first crest value (first amplitude) I1 with time and the state to perform the constant current control in which the electric current I is constantly kept at the second crest value (second amplitude) I2 with time. According to the present modification, in the second output mode, the electric current I supplied to the ultrasonic transducer 22 continuously has the second crest value I2 with time. In the second output mode, the electric current I has only to continuously has a crest value equal to or more than the second crest value I2 with time. For example, according to a certain different modification, in the second output mode, the electric current I is kept at a constant crest value higher than the second crest value I2.

As described above, the electric current T continuously has the second crest value I2 with time in the second output mode, whereas the electric current I supplied to the ultrasonic transducer 22 intermittently has the first crest value I1 lower than the second crest value I2 in the first output mode. Thus, the electric current I supplied to the ultrasonic vibrator (vibration generator) 22 during the unit time ΔT is higher in the second output mode than in the first output mode. Therefore, the electric power P supplied to the ultrasonic transducer (drive force generation unit) 22 during the unit time ΔT is higher in the second output mode than in the first output mode due to, for example, the relation shown in Equation (1) mentioned above.

The amplitude of the longitudinal vibration in the treatment portion 13 (e.g. the protruding end of the protrusion 15) is higher in the state in which the electric current I has the second crest value I2 than in the state in which the electric current I has the first crest value I1. Therefore, the movement distance (movement amount) of the treatment portion 13 in the longitudinal direction parallel to the longitudinal axis C during the unit time ΔT is greater in the second output mode in which the electric current I continuously has the second crest value I2 with time than in the first output mode.

In the fourth modification shown in FIG. 12, as in the third modification, in the first output mode, the electric current I supplied to the ultrasonic transducer 22 alternately changes to the first crest value (first amplitude) I1 and the second crest value (second amplitude) I2 higher than the first crest value I1 with time. However, according to the present modification, in the second output mode, the electric current I alternately changes to the first crest value I1 and a third crest value (third amplitude) I3 higher than the second crest value I2 with time. In the first output mode, the control section 41 controls the output state of the electric power P from the energy supply section 26 by alternately repeating with time the state to perform the constant current control in which the electric current I is constantly kept at the first crest value I1 with time and the state to perform the constant current control in which the electric current I is constantly kept at the second crest value I2 with time. In the second output mode, the controller 41 controls the output state of the electric power P from the energy supplier 26 by alternately repeating with time the state to perform the constant current control in which the electric current I is constantly kept at the first crest value I1 with time and the state to perform the constant current control in which the electric current I is constantly kept at the third crest value I3 with time.

As described above, the electric current I supplied to the ultrasonic transducer 22 intermittently has the second crest value I2 with time in the first output mode, whereas the electric current I intermittently has the third crest value I3 higher than the second crest value I2 in the second output mode. Thus, the electric current I supplied to the ultrasonic transducer (vibration generation section) 22 during the unit time ΔT is higher in the second output mode than in the first output mode. Therefore, the electric power P supplied to the ultrasonic transducer (drive force generation unit) 22 during the unit time ΔT is higher in the second output mode than in the first output mode due to, for example, the relation shown in Equation (1) mentioned above.

Amplitude U3 of the treatment portion 13 (e.g. the protruding end of the protrusion 15) in which the electric current I has the third crest value I3 is higher than the amplitude U2 of the treatment portion 13 in which the electric current I has the second crest value I2. Thus, the movement distance (movement amount) of the treatment portion 13 (e.g. the protruding end of the protrusion 15) in the longitudinal direction parallel to the longitudinal axis C during the unit time ΔT is greater in the second output mode of the energy supply section 26 than in the first output mode.

In the fifth modification shown in FIG. 13, in the first output mode and the second output mode, the electric current I supplied to the ultrasonic transducer 22 alternately changes to the first crest value (first amplitude) I1 and the second crest value (second amplitude) I2 higher than the first crest value I1 with time. Therefore, in the first output mode and the second output mode, the control section 41 controls the output state of the electric power P from the energy supply section 26 by alternately repeating with time the state to perform the constant current control in which the electric current I is constantly kept at the first crest value I1 with time and the state to perform the constant current control in which the electric current I is constantly kept at the second crest value I2 with time. However, according to the present modification, the ratio of a time Δw2 in which the electric current I has the second crest value I2 during the unit time ΔT in the second output mode is higher than the ratio of a time Δw1 in which the electric current I has the second crest value I2 during the unit time ΔT in the first output mode. That is, the duty ratio (Δw1/ΔT or Δw2/ΔT) of the time (Δw1 or Δw2) at the second crest value I2 during the unit time ΔT is higher in the second output mode than in the first output mode.

As described above, the ratio (duty ratio) of the time (Δw1 or Δw2) in which the electric current I has the second crest value I2 higher than the first crest value I1 during the unit time ΔT is higher in the second output mode than in the first output mode. Thus, the electric current I supplied to the ultrasonic transducer (vibration generator) 22 during the unit time ΔT is higher in the second output mode than in the first output mode. Therefore, the electric power P supplied to the ultrasonic vibrator (drive force generation unit) 22 during the unit time ΔT is higher in the second output mode than in the first output mode due to, for example, the relation shown in Equation (1) mentioned above.

The amplitude U2 of the treatment portion 13 (e.g. the protruding end of the protrusion 15) in which the electric current I has the second crest value I2 is higher than the amplitude U1 of the treatment portion 13 in which the electric current I has the first crest value I1. Accordingly, the ratio of the time in which the treatment portion 13 oscillates with the amplitude U2 during the unit time ΔT is higher in the second output mode than in the first output mode. Thus, the movement distance (movement amount) of the treatment portion 13 (e.g. the protruding end of the protrusion 15) in the longitudinal direction parallel to the longitudinal axis C during the unit time ΔT is greater in the second output mode of the energy supply section 26 than in the first output mode.

In the first embodiment and the first modification to the fifth modification described above, the electric power P supplied to the ultrasonic transducer (drive force generation unit) 22 during the unit time ΔT is higher in the second output mode than in the first output mode. Thus, the electric current I supplied to the ultrasonic vibrator (vibration generation section) 22 during the unit time ΔT is higher in the second output mode than in the first output mode. Because the electric current I supplied to the ultrasonic transducer 22 is higher, the movement distance (movement amount) of the treatment portion 13 (e.g. the protruding end of the protrusion 15) in the longitudinal direction parallel to the longitudinal axis C during the unit time ΔT is greater in the second output mode than in the first output mode. The control described above is performed to switch the output state of the electric power from the energy supply section 26 to the second output mode and increase the movement distance of the treatment portion 13 in the longitudinal direction during the unit time ΔT even when the treatment portion has bitten in the hard tissue. Consequently, the biting of the treatment portion 13 into the hard tissue is appropriately eliminated.

Second Embodiment

Figure 14:
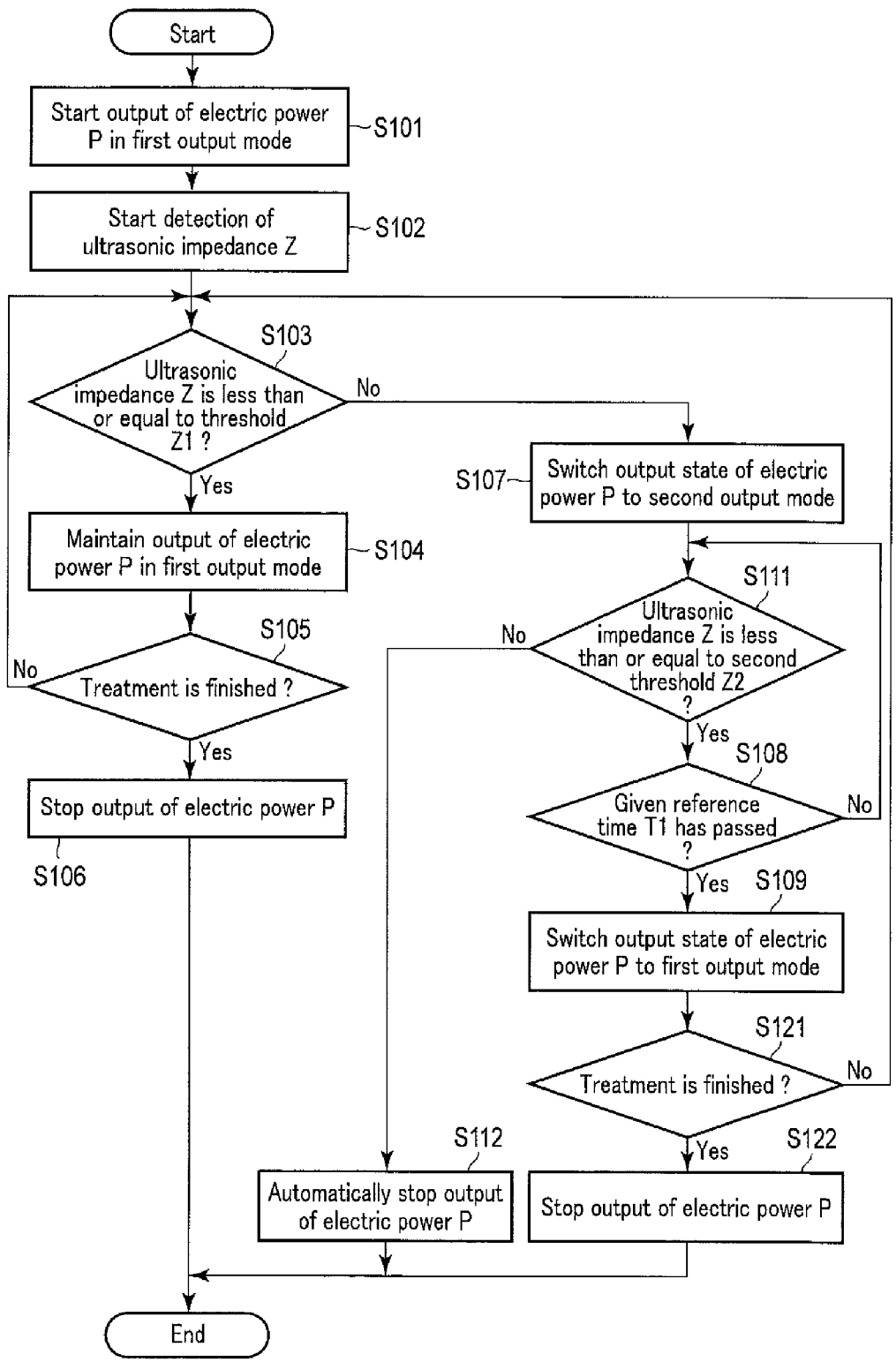
FIG. 14 is a flowchart showing processing in a treatment by the energy source unit according to the second embodiment.

Next, a second embodiment of the present invention is described with reference to FIG. 14 and FIG. 15. In the second embodiment, the configuration according to the first embodiment is modified as follows. The same parts as those in the first embodiment are indicated by the same reference marks and are not described.

In the present embodiment, processing in the energy source unit 3 in a treatment (e.g. a treatment to shave a hard tissue) is different from that in the first embodiment. FIG. 14 is a flowchart showing the processing in the energy source unit 3 in the treatment. As shown in FIG. 14, steps S101 to S109, S121, and S122 described above in the first embodiment are also performed in the present embodiment. However, in the present modification, if it is judged that the ultrasonic impedance Z is higher than a first threshold (threshold) Z1 (step S103—no) and the output state of the electric power P from the energy supply section 26 is switched to the second output mode from the first output mode (step S107), the judgment section 45 judges with time whether the ultrasonic impedance Z is less than or equal to a second threshold Z2 (step S111). Here, the first threshold Z1 corresponds to the threshold Z1 in the first embodiment, and the second threshold Z2 is higher than the first threshold Z1. Therefore, in the present embodiment, it is judged whether the ultrasonic impedance Z (i.e. the load on the ultrasonic probe 9) is less than or equal to the second threshold Z2 higher than the first threshold Z1 while the electric power P is being output from the energy supplier 26 in the second output mode.

Whether the ultrasonic impedance Z is less than or equal to the second threshold Z2 is judged (step S111) continuously with time until the given reference time T1 passes after the switch of the output state of the electric power P from the energy supply section 26 to the second output mode (step S108—no). When the ultrasonic impedance Z is continuously less than or equal to the second threshold Z2 with time until the given reference time T1 passes after the switch to the second output mode (step 111—yes and step S108—yes), the control section 41 switches the output state of the electric power P from the energy supply section 26 from the second output mode to the first output mode (step S109).

In contrast, when it is judged that the ultrasonic impedance Z is more than the second threshold Z2 until the given reference time T1 passes after the switch to the second output mode (step S111—no), the control section 41 automatically stops the output of the electric power P from the energy supply section 26 (step S112). That is, in the present embodiment, when the judgment section 45 judges that the load on the ultrasonic probe 9 (the ultrasonic impedance Z) is more than the second threshold (Z2) after the switch of the output state of the electric power P from the energy supply section 26 to the second output mode, the output of the electric power P from the energy supply section 26 is stopped. In other words, as soon as the ultrasonic impedance Z surpasses the second threshold Z2, the controller 41 stops the output of the electric power P from the energy supply section 26 regardless of whether an input is made with the energy operation input button 12 (whether the energy operation input button 12 is released). Accordingly, the electric power P is not supplied to the ultrasonic transducer 22, and no ultrasonic vibration is generated. Thus, the ultrasonic probe 9 does not longitudinally vibrate, and no ultrasonic vibration is transmitted to the treatment portion 13.

FIG. 15 is a diagram showing an example of changes of the ultrasonic impedance Z detected by the impedance detection section 42 with time which is different from that in each of FIG. 7 and FIG. 8. In FIG. 15, the ultrasonic impedance Z is indicated on the vertical axis, and time t is indicated on the horizontal axis. In FIG. 15, the output of the electric power P from the energy supply section 26 is started at a time t9.

In FIG. 15, the ultrasonic impedance Z becomes higher than the first threshold Z1 at a time t10 due to, for example, the biting into the hard tissue (treated target). Accordingly, the control section 41 switches the output state of the electric power P from the energy supply section 26 from the first output mode to the second output mode at the time t10. However, the biting of the treatment portion 13 into the hard tissue may not be eliminated even when the movement distance of the treatment portion 13 in the longitudinal direction during the unit time ΔT is increased by the switch to the second output mode. If the treatment portion 13 is vibrated without the elimination of the biting into the hard tissue, the ultrasonic treatment instrument 2 including the ultrasonic probe 9 may be broken, or parts of the hard tissue other than the treated target may be damaged.

When the treatment portion 13 is vibrated without the elimination of the biting into the hard tissue, the load on the ultrasonic probe 9 further increases. Therefore, the ultrasonic impedance Z which has become higher than the first threshold Z1 further increases. In FIG. 15, even after the switch to the second output mode at the time t10, the biting of the treatment portion 13 into the hard tissue is not eliminated, and the ultrasonic impedance Z which is higher than the first threshold Z1 further increases.

At a time t11, the ultrasonic impedance Z becomes higher than the second threshold Z2. In the present embodiment, whether the ultrasonic impedance Z is less than or equal to the second threshold Z2 is judged with time while the electric power P is being output from the energy supply section 26 in the second output mode, and the output of the electric power P is stopped if the ultrasonic impedance Z becomes higher than the second threshold Z2. Thus, in one example of FIG. 15, the control section 41 automatically stops the output of the electric power P from the energy supply section 26 at the time t11 at which the ultrasonic impedance Z becomes higher than the second threshold Z2.

The output state of the electric power P is controlled as described above, so that in the present embodiment, the treatment portion 13 is prevented from vibrating (longitudinally vibrating) without the elimination of the biting into the hard tissue. This effectively prevents the ultrasonic treatment instrument 2 including the ultrasonic probe 9 from being broken, and also effectively prevents parts of the hard tissue other than the treated target from being damaged.

Third Embodiment

Figure 16:
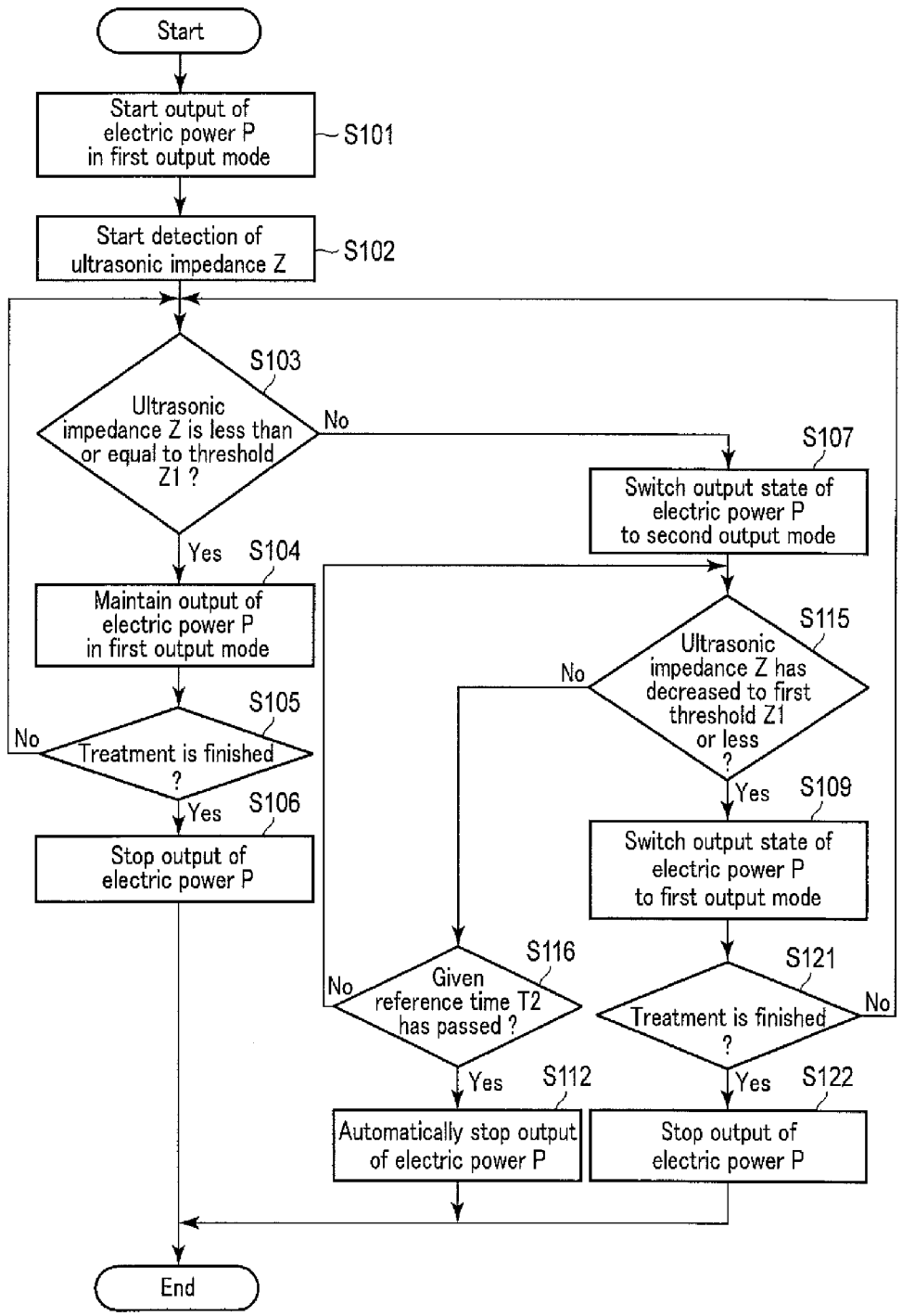
FIG. 16 is a flowchart showing processing in a treatment by the energy source unit according to a third embodiment.

Next, a third embodiment of the present invention is described with reference to FIG. 16 to FIG. 18. In the third embodiment, the configuration according to the first embodiment is modified as follows. The same parts as those in the first embodiment are indicated by the same reference marks and are not described.

In the present embodiment, processing in the energy source unit 3 in a treatment (e.g. a treatment to abrade a hard tissue) is different from that in the first embodiment. FIG. 16 is a flowchart showing the processing in the energy source unit 3 in the treatment. As shown in FIG. 16, steps S101 to S107, S109, S121, and S122 described above in the first embodiment are also performed in the present embodiment. However, in the present modification, step S108 in the first embodiment is not performed. In the present embodiment, if it is judged that the ultrasonic impedance Z is higher than the threshold (first threshold) Z1 (step S103—no) and the output state of the electric power P from the energy supply section 26 is switched to the second output mode from the first output mode (step S107), the judgment section 45 judges with time whether the ultrasonic impedance Z has decreased to the threshold Z1 or less (step S115). That is, the judgment section 45 judges with time whether the load on the ultrasonic probe 9 (i.e. the ultrasonic impedance Z) is less than or equal to the threshold (first threshold) Z1 while the electric power is being output from the energy supplier 26 in the second output mode.

Whether the ultrasonic impedance Z is less than or equal to the threshold Z1 is judged (step S115) continuously with time until the given reference time T2 passes after the switch of the output state of the electric power P from the energy supply section 26 to the second output mode (step S116—no). When the ultrasonic impedance Z has decreased to the threshold (first threshold) Z1 or less while the given reference time T2 passes after the switch to the second output mode (step S115—yes), the control section 41 switches the output state of the electric power P from the energy supply section 26 from the second output mode to the first output mode (step S109). That is, when the judgment section 45 judges that the load on the ultrasonic probe 9 (the ultrasonic impedance Z) is less than or equal to the threshold (Z1) after the switch of the output state of the electric power P to the second output mode, the output state of the electric power P from the energy supply section 26 is again switched to the first output mode.

In contrast, when the ultrasonic impedance Z is continuously more than the threshold (first threshold) Z1 until the given reference time T2 passes after the switch to the second output mode (step S115—no and step S116—yes), the control section 41 maintains the output state of the electric power P in the second output mode for the given reference time T2 after the switch to the second output mode. At the point where the given reference time T2 has passed since the switch to the second output mode, the output of the electric power P from the energy supply section 26 is automatically stopped (step S112). That is, when the electric power P is continuously output for the given reference time T2 in the second output mode after the output state of the electric power P from the energy supply section 26 is switched to the second output mode, the control section 41 stops the output of the electric power P from the energy supplier 26.

The given reference time T2 in the present embodiment may have the same length as that of the given reference time T1 in the first embodiment, or may have a length different from that of the given reference time T1 in the first embodiment. The given reference time T2 is, for example, 0.5 seconds to 1.0 second.

FIG. 17 is a diagram showing an example of changes of the ultrasonic impedance Z detected by the impedance detection section 42 with time which is different from that in each of FIG. 7, FIG. 8, and FIG. 15. In FIG. 17, the ultrasonic impedance Z is indicated on the vertical axis, and time t is indicated on the horizontal axis. In FIG. 17, the output of the electric power P from the energy supply section 26 is started at a time t12, and the output of the electric power P from the energy supply section 26 is stopped at a time t13.

In FIG. 17, the ultrasonic impedance Z becomes higher than the threshold (first threshold) Z1 at a time t14 due to, for example, the biting into the hard tissue (treated target). Accordingly, the control section 41 switches the output state of the electric power P from the energy supply section 26 from the first output mode to the second output mode at the time t14. In FIG. 17, the biting of the treatment portion 13 into the hard tissue is eliminated in the vicinity of a time t15. As a result, the ultrasonic impedance Z decreases to the threshold Z1 or less at the time t15. That is, the ultrasonic impedance Z again becomes the threshold Z1 or less before the given reference time T2 passes from the time t14 at which the output mode is switched to the second output mode.

The ultrasonic impedance Z becomes the threshold Z1 or less so that the control section 41 again switches the output state of the electric power P from the energy supply section 26 from the second output mode to the first output mode at the time t15. The electric power P is continuously output in the first output mode with time from the time t15 to the time t13.

As described above, the movement distance of the treatment portion 13 in the longitudinal direction during the unit time ΔT is greater when the electric power P is output in the second output mode than when the electric power P is output in the first output mode. Thus, the movement velocity of the treatment portion 13 (the ultrasonic probe 9) is higher and the ultrasonic probe 9 is more easily damaged in the second output mode than in the first output mode. Accordingly, in the present embodiment, the ultrasonic impedance Z (the load on the ultrasonic probe 9) is detected with time even after the switch to the second output mode. If the ultrasonic impedance Z decreases to the threshold Z1 or less, the output state of the electric power P is again switched to the first output mode.

The output state of the electric power P is controlled as described above, so that in the present embodiment, the output mode is quickly switched to the first output mode from the second output mode in response to the changes of the ultrasonic impedance Z (the load on the ultrasonic probe 9) with time even when the electric power P is output in the second output mode. This effectively prevents the ultrasonic probe 9 from being damaged.

FIG. 18 is a diagram showing an example of changes of the ultrasonic impedance Z detected by the impedance detection section 42 with time which is different from that in each of FIG. 7, FIG. 8, FIG. 15, and FIG. 17. In FIG. 18, the ultrasonic impedance Z is indicated on the vertical axis, and time t is indicated on the horizontal axis. In FIG. 18, the output of the electric power P from the energy supply section 26 is started at a time t16.

In FIG. 18, the ultrasonic impedance Z becomes higher than the threshold (first threshold) Z1 at a time t17 due to, for example, the biting into the hard tissue (treated target). Accordingly, the control section 41 switches the output state of the electric power P from the energy supply section 26 from the first output mode to the second output mode at the time t17. However, in FIG. 18, the biting of the treatment portion 13 into the hard tissue is not eliminated even when the movement distance of the treatment portion 13 in the longitudinal direction during the unit time ΔT is increased by the switch to the second output mode. Thus, the treatment portion 13 still bites into the hard tissue even if the given reference time T2 passes after the time t17 at which the output state of the electric power P is switched to the second output mode. Therefore, the ultrasonic impedance Z is continuously more than the threshold Z1 with time until the given reference time T2 passes from the time t17.

In the present embodiment, when the ultrasonic impedance Z is continuously more than the threshold (first threshold) Z1 until the given reference time T2 passes after the switch to the second output mode, the output of the electric power P from the energy supplier 26 is stopped. Therefore, in FIG. 18, the output of the electric power P is automatically stopped at the time t17+T2.

The output state of the electric power P is controlled as described above, so that in the present embodiment, the treatment portion 13 is prevented from continuously vibrating (longitudinally vibrating) without the elimination of the biting into the hard tissue. This effectively prevents the ultrasonic treatment instrument 2 including the ultrasonic probe 9 from being broken, and also effectively prevents parts of the hard tissue other than the treated target from being damaged.

Fourth Embodiment

Figure 19:
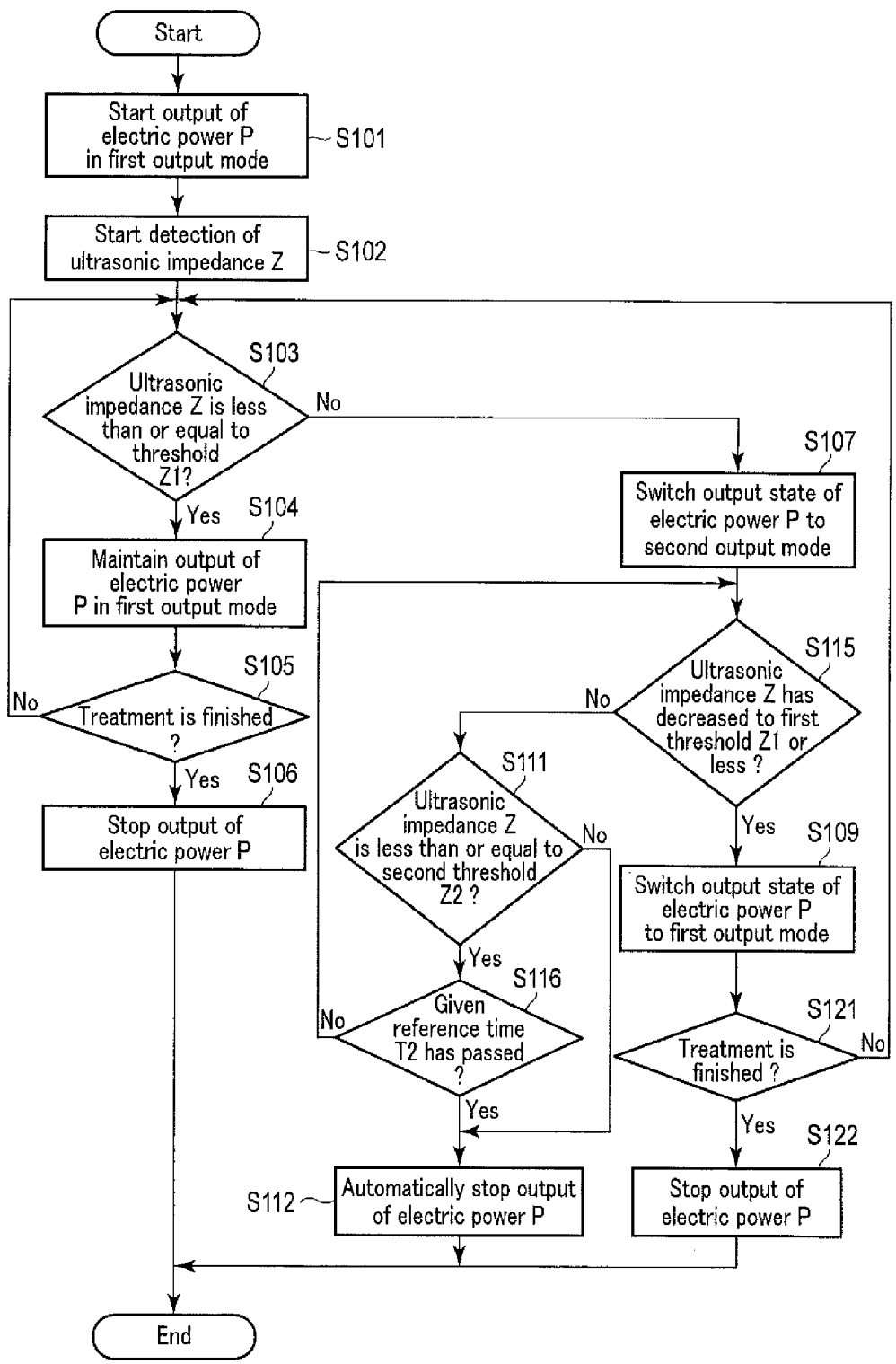
FIG. 19 is a flowchart showing processing in a treatment by the energy source unit according to a fourth embodiment.

Next, a fourth embodiment of the present invention is described with reference to FIG. 19. In the fourth embodiment, the configuration according to the third embodiment is modified as follows. The same parts as those in the third embodiment are indicated by the same reference marks and are not described.

In the present embodiment, processing in the energy source unit 3 in a treatment (e.g. a treatment to shave a hard tissue) is different from that in the third embodiment. However, the processing in the energy source unit 3 according to the present embodiment is merely a combination of the processing in the third embodiment and the processing in step S111 according to the second embodiment. FIG. 19 is a flowchart showing processing in the energy source unit 3 in a treatment.

In the present embodiment, if it is judged that the ultrasonic impedance Z is higher than the threshold (first threshold) Z1 (step S103—no) and the output state of the electric power P from the energy supply section 26 is switched to the second output mode from the first output mode (step S107), the judgment section 45 judges with time whether the ultrasonic impedance Z has decreased to the threshold Z1 or less (step S115), and also judges whether the ultrasonic impedance Z is less than or equal to the second threshold Z2 (step S111). In the present embodiment as well as in the second embodiment, the first threshold Z1 corresponds to the threshold Z1 in the first embodiment, and the second threshold Z2 is higher than the first threshold Z1.

Whether the ultrasonic impedance Z is less than or equal to the first threshold Z1 is judged (step S115) and whether the ultrasonic impedance Z is less than or equal to the second threshold Z2 is judged (step S111) continuously with time until the given reference time T2 passes after the switch of the output state of the electric power P from the energy supply section 26 to the second output mode (step S116—no). When the ultrasonic impedance Z has decreased to the first threshold Z1 or less while the given reference time T2 passes after the switch to the second output mode (step S115—yes), the control section 41 switches the output state of the electric power P from the energy supply section 26 from the second output mode to the first output mode as in the third embodiment (step S109).

When the ultrasonic impedance Z has become higher than the second threshold Z2 while the given reference time T2 passes after the switch to the second output mode (step S115—no and step S111—no), the output of the electric power P from the energy supply section 26 is automatically stopped (step S112). When the ultrasonic impedance Z is continuously less than or equal to the second threshold Z2 during the given reference time T2 (step S111—yes) but when the ultrasonic impedance Z is continuously more than the first threshold Z1 with time until the given reference time T2 passes after the switch to the second output mode (step S115—no and step S116—yes), the output of the electric power P from the energy supply section 26 is automatically stopped at the point where the given reference time T2 has passed since the switch to the second output mode as in the third embodiment (step S112).

The output state of the electric power P is controlled as described above, so that in the present embodiment, when the ultrasonic impedance Z changes with time as shown in FIG. 17, the output state of the electric power P is switched to the first output mode from the second output mode before the given reference time T2 passes from the time t14 at which the output mode is switched to the second output mode (time t15). When the ultrasonic impedance Z changes as shown in FIG. 18, the output of the electric power P is automatically stopped at the time t17+T2. In the present embodiment, when the ultrasonic impedance Z changes as shown in FIG. 15, the output of the electric power P is automatically stopped before the given reference time T2 passes from the time t10 at which the output mode is switched to the second output mode (time t11).

The present embodiment has the functions and advantageous effects similar to those in the embodiments described above.

Modifications of First Embodiment to Fourth Embodiment

Although the output of the electric power P is automatically stopped in step S112 in the second embodiment to the fourth embodiment, this is not a limitation. Instead of step S112, the control section 41 may switch the output state of the electric power P from the energy supply section 26 to a third output mode in which the electric power P that is supplied to the ultrasonic transducer (drive force generation unit) 22 during the unit time ΔT is lower than that in the first output mode. In this case, the input of the energy operation in the energy operation input button 12 is stopped. Accordingly, the output (supply) of the electric power P to the ultrasonic transducer (drive force generation unit) 22 from the energy supply section 26 is stopped. The electric power P supplied to the ultrasonic vibrator 22 during the unit time ΔT decreases, so that in the third output mode, the electric current I supplied to the ultrasonic transducer 22 during the unit time ΔT is lower than in the first output mode. As a result, the movement distance of the treatment portion 13 in the longitudinal direction during the unit time ΔT is smaller and the movement velocity (vibration velocity) of the treatment portion 13 is lower in the third output mode than in the first output mode.

In a certain modification, a notifying section (not shown) such as a buzzer, a lamp, or a display may be provided, and the stopping of the output of the electric power P may be notified to, for example, a surgeon by the notifying section instead of step S112. The method of notifying includes, for example, sound emission by the buzzer, lighting of the lamp, or an indication on the display.

The matters described in the modifications of the first embodiment can also be suitably modified in each of the second to fourth embodiments.

In the first embodiment to the fourth embodiment and the modifications thereof, the control section (41) is configured to control the output state of the electric power (P) from the energy supply section (26) so that the electric current (I) supplied to the ultrasonic transducer (22) of the drive force generation unit (22) during the unit time ($\Delta T$) is higher in the second output mode than in the first output mode. Thus, the electric power (P) supplied to the drive force generation unit (22) during the unit time ($\Delta T$) is higher in the second output mode than in the first output mode.

Fifth Embodiment

Figure 20:
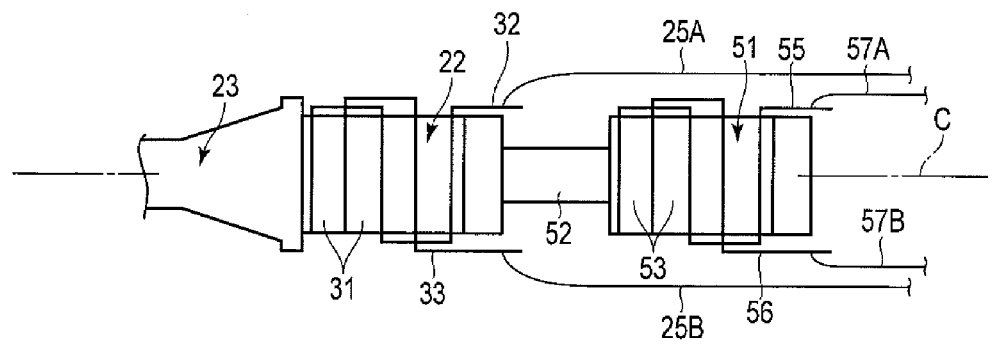
FIG. 20 is a schematic diagram showing the configuration of a drive force generation unit according to a fifth embodiment.

Next, a fifth embodiment of the present invention is described with reference to FIG. 20 to FIG. 22. In the fifth embodiment, the configuration according to the first embodiment is modified as follows. The same parts as those in the first embodiment are indicated by the same reference marks and are not described.

In the present embodiment, the drive force generation unit which actuates the ultrasonic probe 9 is formed by an actuator section 51 in addition to the ultrasonic transducer (vibration generation section) 22. FIG. 20 is a diagram showing the drive force generation unit (the ultrasonic transducer 22 and the actuator section 51) according to the present embodiment. In the present embodiment, a connection component 52 is connected to the proximal side of the horn component 23, and the actuator section 51 is attached to the connection component 52. In a certain example, the ultrasonic vibration generated in the ultrasonic transducer 22 is transmitted to the connection component 52, and the connection component 52 vibrates (longitudinally vibrates) by the ultrasonic vibration together with the ultrasonic probe 9 and the horn component 23. In this case, the vibration transmission portion which transmits the ultrasonic vibration generated in the ultrasonic transducer 22 is formed by the connection component 52 in addition to the horn component 23 and the ultrasonic probe 9. In another certain example, the ultrasonic vibration generated in the ultrasonic vibrator 22 is not transmitted to the connection component 52, and the connection component 52 does not vibrate together with the ultrasonic probe 9 and the horn component 23. However, in each case, the drive force (movement drive force) generated in the actuator section 51 is transmitted to the horn component 23 and the ultrasonic probe 9.

In the present embodiment, the actuator section 51 is, for example, an impact transducer, and includes piezoelectric elements 53. The actuator section 51 includes a third electrode portion 55 and a fourth electrode portion 56. One end of an electric power supply path 57A formed from, for example, an electric wire is connected to the third electrode portion 55, and one end of an electric power supply path 57B formed from, for example, an electric wire is connected to the fourth electrode portion 56. The electric power supply paths 57A and 57B extend through a inside of the cable 7, and have the other ends connected to the energy supply section 26 of the energy source unit 3.

Figure 21:
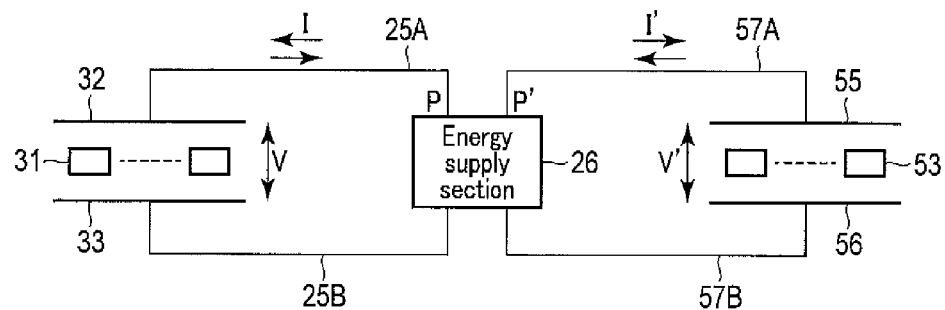
FIG. 21 is a schematic diagram showing an electric connection state between the energy supply section and the drive force generation unit according to the fifth embodiment.

FIG. 21 is a diagram showing an electric connection state between the energy supply section 26 and the drive force generation unit (the ultrasonic transducer 22 and the actuator section 51). As shown in FIG. 20 and FIG. 21, in the present embodiment, the electric power P is configured to be supplied to the ultrasonic transducer 22 from the energy supply section 26 through the electric power supply paths 25A and 25B, and electric power P' is configured to be supplied to the actuator section 51 from the energy supply section 26 through the electric power supply paths 57A and 57B. Therefore, the energy supply section 26 is configured to output the electric power P which is supplied to the ultrasonic vibrator 22, and also configured to output the electric power P' which is supplied to the actuator section 51.

In the present embodiment as well as in the embodiments described above, changes of the load on the ultrasonic probe 9 (the ultrasonic impedance Z) with time are detected. The control section 41 then controls the output state of the electric power (P, P') from the energy supply section 26 on the basis of the detection result of the load on the ultrasonic probe 9, as in the embodiments described above. That is, in the present embodiment as well as in the embodiments described above, the switch between the first output mode and the second output mode is made on the basis of the detection result of the load on the ultrasonic probe 9.

However, in the present embodiment, the electric power P supplied to the ultrasonic transducer 22 does not vary between the first output mode and the second output mode. That is, for example, the crest value and duty ratio of the electric current I supplied to the ultrasonic transducer 22 do not vary between the first output mode and the second output mode, and the intensity of the electric current I supplied to the ultrasonic vibrator 22 during the unit time $\Delta T$ is the same in the first output mode and the second output mode.

In the present embodiment, in the first output mode, the electric power P is supplied to the ultrasonic transducer (vibration generator) 22 alone from the energy supply section 26, and the electric power P' is not supplied to the actuator section 51. In contrast, in the second output mode, the electric power P is supplied to the ultrasonic transducer 22, and the electric power P' is supplied to the actuator section 51. Therefore, in the drive force generation unit formed from the ultrasonic transducer 22 and the actuator section 51, an electric power (P+P') supplied from the energy supply section 26 during the unit time $\Delta T$ in the second output mode is higher than the electric power P supplied from the energy supply section 26 during the unit time $\Delta T$ in the first output mode.

By the supply of the electric power P, the electric current I which is, for example, a sinusoidal alternating electric current and a continuous-wave electric current flows through the piezoelectric elements 31 of the ultrasonic transducer 22. As a result, as in the embodiments described above, an ultrasonic vibration is generated in the ultrasonic transducer 22, and the ultrasonic probe 9 longitudinally vibrates by the ultrasonic vibration.

A voltage V' is applied across the third electrode portion 55 and the fourth electrode portion 56 by the output of the electric power P' to the actuator section 51 from the energy supply section 26. By the application of the voltage V', an electric current (drive force generation electric current) I' flows through the piezoelectric elements 53 between the third electrode portion 55 and the fourth electrode portion 56.

Figure 22:
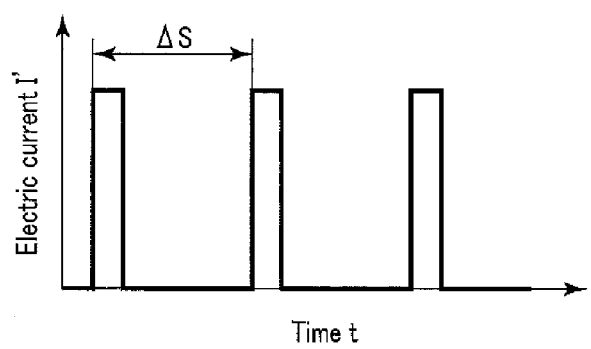
FIG. 22 is a schematic diagram showing an example of changes with time of an electric current which flows through piezoelectric elements of an actuator section in a second output mode in which an electric power is supplied to the actuator section according to a fifth embodiment.

FIG. 22 is a diagram showing an example of changes with time of the electric current I' which flows through the piezoelectric elements 53 of the actuator section 51 in the second output mode in which the electric power P' is supplied to the actuator section 51. In FIG. 22, the crest value of the electric current I' is indicated on the vertical axis, and time t is indicated on the horizontal axis. As shown in FIG. 22, in the second output mode in which the electric power P' is supplied to the actuator section 51, the electric current I' instantaneously and intermittently flows through the piezoelectric elements 53 of the actuator section 51, and the electric current I' is a pulse-wave electric current. That is, the controller 41 controls the output state of the electric power P' from the energy supply section 26 so that the electric current I' instantaneously flows through the piezoelectric elements 53 at a predetermined time period ΔS.

A drive force is generated in the actuator section 51 by the flow of the electric current I' through the piezoelectric elements 53. The drive force generated in the actuator section 51 is transmitted to the ultrasonic probe 9 via the horn component 23. The ultrasonic probe 9 including the treatment portion 13 moves in the longitudinal direction parallel to the longitudinal axis C by the transmission of the drive force (movement drive force) to the ultrasonic probe 9.

Here, in the second output mode, the ultrasonic vibration is generated in the ultrasonic transducer 22, and the ultrasonic probe 9 longitudinally vibrates. When the drive force is generated in the actuator section 51, the generated drive force is transmitted to the ultrasonic probe 9 regardless of whether the ultrasonic vibration is generated in the ultrasonic transducer 22. Therefore, in the second output mode of the energy supply section 26, the ultrasonic probe 9 (the treatment portion 13) instantaneously and intermittently moves in the longitudinal direction by the movement drive force generated in the actuator section 51 simultaneously with the longitudinal vibration of the ultrasonic probe 9 (the treatment portion 13) by the ultrasonic vibration.

The output state of the electric power (P, P') from the energy supply section 26 is controlled in the first output mode and the second output mode as described above, so that the treatment portion 13 only longitudinally vibrates by the ultrasonic vibration in the first output mode. In contrast, in the second output mode, the treatment portion 13 not only longitudinally vibrates by the ultrasonic vibration but also intermittently moves in the direction parallel to the longitudinal axis C by the drive force (movement drive force) generated in the actuator section 51. Thus, the movement distance (movement amount) of the treatment portion 13 (e.g. the protruding end of the protrusion 15) in the longitudinal direction parallel to the longitudinal axis C during the unit time ΔT is greater in the second output mode of the energy supply section 26 than in the first output mode. Therefore, in the present embodiment as well as in the first embodiment, even when the treatment portion 13 has bitten in (has been caught in) the hard tissue, the biting of the treatment portion 13 into the hard tissue can be appropriately eliminated.

Modification of Fifth Embodiment

Although the electric power P supplied to the ultrasonic transducer 22 does not vary between the first output mode and the second output mode in the fifth embodiment, this is not a limitation. For example, as has been described above in the first embodiment and the modifications thereof, the electric power P (the electric current I) supplied to the ultrasonic transducer 22 may vary between the first output mode and the second output mode. However, in this case as well, the electric power P is supplied to the ultrasonic vibrator (vibration generation section) 22 alone in the first output mode, and the electric power (P+P') is supplied to the actuator section 51 as well as to the ultrasonic transducer 22 in the second output mode.

Although the actuator section 51 is formed from the piezoelectric elements 53 in the fifth embodiment, this is not a limitation. For example, the actuator section 51 may be an electric motor which is driven by the supply of the electric power P'.

That is, in the fifth embodiment and the modifications thereof, the drive force generation unit is formed by the actuator section (51) in addition to the vibration generation section (22). A movement drive force different from the ultrasonic vibration is generated by the supply of the electric power (P') to the actuator section (51). The generated movement drive force is transmitted to the ultrasonic probe (9) regardless of whether the ultrasonic vibration is generated in the vibration generation section (22). As a result, the ultrasonic probe (9) moves in the direction parallel to the longitudinal axis (C).

In the fifth embodiment and the modifications thereof, the control section (41) controls the output state of the electric power (P, P') from the energy supply section (26) so that the electric power (P) is supplied to the vibration generation section (22) alone in the first output mode and so that the electric power (P, P') is supplied to the actuator section (51) as well as to the vibration generation section (22) in the second output mode. Thus, the electric power (P, P') supplied to the vibration generation section (22) during the unit time (ΔT) is higher in the second output mode than in the first output mode.

Other Modifications

Although the load on the ultrasonic probe 9 is detected with time by detecting changes of the ultrasonic impedance Z with time in the embodiments described above, this is not a limitation. For example, as shown in a modification of the embodiments described above in FIG. 23, a force amount detection section 61 such as a force amount sensor may be provided instead of the impedance detection section 42. In the present modification, the force amount detector 61 is attached to the cylindrical case 11 of the holding unit 6. The force amount detection section 61 has only to be attached to the ultrasonic treatment instrument 2, and may be attached to, for example, the sheath 8.

One end of a signal path portion 62 is connected to the force amount detection section 61. The signal path portion 62 extends through the transducer case 21 and an inside of the cable 7, and has the other end connected to the control section 41. The force amount detector 61 is configured to detect the load on the ultrasonic probe 9 with time by detecting the amount of force on the ultrasonic treatment instrument 2 with time. If the load on the ultrasonic probe 9 increases, the amount of force which is applied by, for example, a surgeon also increases. Therefore, the amount of force applied to the ultrasonic treatment instrument 2 changes in response to the load on the ultrasonic probe 9.

A detection signal which indicates a detection result of changes of the amount of force applied to the ultrasonic treatment instrument 2 (i.e. the load on the ultrasonic probe 9) with time is transmitted to the control section 41 through the signal path portion 62. On the basis of the detection signal, the judgment section 45 judges in a manner similar to that in the embodiments described above, and the control section 41 controls the output state of the electric power P from the energy supply section 26 in a manner similar to that in the embodiments described above.

Although the treatment portion 13 is an L-shaped hook in the embodiments described above, this is not a limitation. For example, the treatment portion 13 may be a spoon-shaped spatula, or may be a flat blade. Moreover, for example, a jaw (not shown) may be turnably attached to the distal portion of the sheath 8, and the jaw may be openable and closable relative to the treatment portion 13. That is, the shape, dimensions, and others of the treatment portion 13 have only to suit to a treatment in which the treatment portion 13 is used.

In the embodiments described above, the drive force generation unit (22; 22, 51) which is configured to generate a drive force to actuate the ultrasonic probe (9) including ultrasonic vibration by the supply of the electric power (P; P, P') is provided. The vibration generation section (22) which is configured to generate an ultrasonic vibration to be transmitted to the ultrasonic probe (9) by the supply of the electric power (P) is provided in the drive force generation unit (22; 22, 51). The energy supply section (26) can output the electric power (P; P, P') in the first output mode and in the second output mode in which the electric power (P; P, P') supplied to the drive force generation unit (22; 22, 51) during the unit time ($\Delta T$) is higher than in the first output mode. While the ultrasonic probe (9) is transmitting an ultrasonic vibration, the load on the ultrasonic probe (9) is detected by the load detection section (42; 61) with time. While the electric power (P; P, P') is being output from the energy supply section (26) in the first output mode, the judgment section (45) judges with time whether the load on the ultrasonic probe (9) is less than or equal to the first threshold (Z1). When the judgment section (45) judges that the load is less than or equal to the first threshold (Z1), the control section (41) maintains the output state of the electric power (P; P, P') from the energy supply section (26) in the first output mode. When the judgment section (45) judges that the load is more than the first threshold (Z1), the control section (41) switches the output state of the electric power (P; P, P') from the energy supply section (26) to the second output mode.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment system to treat bones comprising:
    an ultrasonic probe which extends along a longitudinal axis, and which is configured to transmit an ultrasonic vibration, the ultrasonic probe including a treatment portion configured to conduct a treatment by use of the transmitted ultrasonic vibration;
    a drive force generation unit which includes a vibration generation section configured to generate the ultrasonic vibration, and which is configured to generate a drive force to actuate the ultrasonic probe;
    an energy supply section which is configured to output an electric power to generate the drive force in the drive force generation unit, the energy supply section having at least a first output mode and a second output mode, the electric power supplied to the drive force generation unit during a unit time being higher in the second output mode than in the first output mode;
    a load detection section which is configured to detect a load on the ultrasonic probe with time while the ultrasonic probe is transmitting the ultrasonic vibration;
    a judgment section which is configured to judge with time whether the load on the ultrasonic probe is less than or equal to a first threshold while the electric power is output from the energy supply section in the first output mode; and
    a control section, the control section being configured to maintain an output state of the electric power from the energy supply section in the first output mode when the judgment section judges that the load is less than or equal to the first threshold, the control section being configured to switch the output state of the electric power from the energy supply section to the second output mode when the judgment section judges that the load is more than the first threshold, the control section being configured to again switch the output state of the electric power to the first output mode, configured to switch the output state of the electric power to a third output mode in which the electric power that is supplied to the drive force generation unit during the unit time is lower than that in the first output mode, or configured to stop an output of the electric power from the energy supply section when a predetermined condition is satisfied after a switch to the second output mode.

2. The ultrasonic treatment system according to claim 1, wherein the control section is configured to again switch the output state of the electric power from the energy supply section to the first output mode when a given reference time has passed since a switch of the output state of the electric power from the energy supply section to the second output mode.

3. The ultrasonic treatment system according to claim 1, wherein the judgment section is configured to judge with time whether the load on the ultrasonic probe is less than or equal to the first threshold while the electric power is output from the energy supply section in the second output mode, and
    the control section is configured to again switch the output state of the electric power from the energy supply section to the first output mode when the judgment section judges that the load is less than or equal to the first threshold after a switch of the output state of the electric power from the energy supply section to the second output mode.

4. The ultrasonic treatment system according to claim 3, wherein when the electric power is continuously output for a given reference time in the second output mode after the output state of the electric power from the energy supply section is switched to the second output mode, the control section is configured to stop an output of the electric power from the energy supply section, or configured to switch the output state of the electric power from the energy supply section to the third output mode in.

5. The ultrasonic treatment system according to claim 1, wherein the judgment section is configured to judge with time whether the load on the ultrasonic probe is less than or equal to a second threshold higher than the first threshold while the electric power is being output from the energy supply section in the second output mode, and
    when the judgment section judges that the load is more than the second threshold after a switch of the output state of the electric power from the energy supply section to the second output mode, the control section is configured to stop an output of the electric power from the energy supply section, or configured to switch the output state of the electric power from the energy supply section to the third output mode.

6. The ultrasonic treatment system according to claim 1, wherein the control section is configured to control the output state of the electric power from the energy supply section so that an electric current supplied to the vibration generation section of the drive force generation unit during the unit time is higher in the second output mode than in the first output mode.

7. The ultrasonic treatment system according to claim 6, wherein the control section is configured to control the output state of the electric power from the energy supply section so that the electric current supplied to the vibration generation section continuously has a first crest value with time in the first output mode and so that the electric current supplied to the vibration generation section continuously or intermittently has a second crest value higher than the first crest value with time in the second output mode.

8. The ultrasonic treatment system according to claim 6, wherein the control section is configured to control the output state of the electric power from the energy supply section so that the electric current supplied to the vibration generation section alternately changes to a first crest value and a second crest value higher than the first crest value with time in the first output mode and so that the electric current supplied to the vibration generation section continuously has a crest value equal to or more than the second crest value with time in the second output mode.

9. The ultrasonic treatment system according to claim 6, wherein the control section is configured to control the output state of the electric power from the energy supply section so that the electric current supplied to the vibration generation section alternately changes to a first crest value and a second crest value higher than the first crest value with time in the first output mode and so that the electric current supplied to the vibration generation section alternately changes to the first crest value and a third crest value higher than the second crest value with time in the second output mode.

10. The ultrasonic treatment system according to claim 6, wherein the control section is configured to control the output state of the electric power from the energy supply section so that the electric current supplied to the vibration generation section alternately changes to a first crest value and a second crest value higher than the first crest value with time in the first output mode and the second output mode and so that a ratio of a time in which the electric current has the second crest value during the unit time is higher in the second output mode than in the first output mode.

11. The ultrasonic treatment system according to claim 1, wherein the drive force generation unit includes an actuator section which is configured to generate a movement drive force different from the ultrasonic vibration to move the ultrasonic probe in a direction parallel to the longitudinal axis by the supply of the electric power, and
the control section is configured to control the output state of the electric power from the energy supply section so that the electric power is supplied to the vibration generation section alone in the first output mode and so that the electric power is supplied to the actuator section as well as to the vibration generation section in the second output mode.

12. The ultrasonic treatment system according to claim 1, wherein the load detection section includes an impedance detection section which is configured to detect an ultrasonic impedance of the electric power supplied to the vibration generation section with time.

13. The ultrasonic treatment system according to claim 1, further comprising an ultrasonic treatment instrument including the ultrasonic probe and the drive force generation unit,
wherein the load detection section includes a force amount detection section which is attached to the ultrasonic treatment instrument, and which is configured to detect an amount of force on the ultrasonic treatment instrument with time.

14. An energy source unit to treat bones, the energy source unit being configured to supply an electric power to a drive force generation unit, the drive force generation unit being configured to generate a drive force to actuate an ultrasonic probe extending along a longitudinal axis, the energy source unit comprising:
an energy supply section which is configured to generate an ultrasonic vibration that is transmitted to a treatment portion of the ultrasonic probe through the ultrasonic probe by supplying the electric power to a vibration generation section of the drive force generation unit, the energy supply section being configured to output the electric power in at least a first output mode and a second output mode, the electric power supplied to the drive force generation unit during a unit time being higher in the second output mode than in the first output mode;
a load detection section which is configured to detect a load on the ultrasonic probe with time while the ultrasonic probe is transmitting the ultrasonic vibration;
a judgment section which is configured to judge with time whether the load on the ultrasonic probe is less than or equal to a threshold while the electric power is output from the energy supply section in the first output mode; and
a control section, the control section being configured to maintaining an output state of the electric power from the energy supply section in the first output mode when the judgment section judges that the load is less than or equal to the threshold, the control section being configured to switch the output state of the electric power from the energy supply section to the second output mode when the judgment section judges that the load is more than the threshold, the control section being configured to again switch the output state of the electric power to the first output mode, configured to switch the output state of the electric power to a third output mode in which the electric power that is supplied to the drive force generation unit during the unit time is lower than that in the first output mode, or configured to stop an output of the electric power from the energy supply section when a predetermined condition is satisfied after a switch to the second output mode.

15. An actuation method of an energy source unit to treat bones, the energy source unit supplying an electric power to a drive force generation unit, the drive force generation unit being configured to generate a drive force to actuate an ultrasonic probe extending along a longitudinal axis, the actuation method comprising:
causing an energy supply section to generate an ultrasonic vibration that is transmitted to a treatment portion of the ultrasonic probe through the ultrasonic probe by supplying the electric power to a vibration generation section of the drive force generation unit;
causing a load detection section to detect a load on the ultrasonic probe with time while the ultrasonic probe is transmitting the ultrasonic vibration;
causing a judgment section to judge with time whether the load on the ultrasonic probe is less than or equal to a threshold while the electric power is output from the energy supply section in a first output mode; and causing a control section to control an output state of the electric power from the energy supply section on the basis of a judgment result in the judgment section, the control section maintaining the output state of the electric power from the energy supply section in the first output mode when the judgment section judges that the load is less than or equal to the threshold, the control section switching the output state of the electric power from the energy supply section to a second output mode when the judgment section judges that the load is more than the threshold, the electric power supplied to the drive force generation unit during a unit time being higher in the second output mode than in the first output mode, the control section again switching the output state of the electric power to the first output mode, switching the output state of the electric power to a third output mode in which the electric power that is supplied to the drive force generation unit during the unit time is lower than that in the first output mode, or stopping an output of the electric power from the energy supply section when a predetermined condition is satisfied after a switch to the second output mode.

* * * * *